US012714741B2

(12) United States Patent
Liu et al.

(10) Patent No.: US 12,714,741 B2
(45) Date of Patent: Aug. 25, 2026

(54) METHOD FOR PREPARING POLYETHYLENE GLYCOL-MODIFIED URATE OXIDASE

(71) Applicant: HANGZHOU GRAND BIOLOGIC PHARMACEUTICAL INC., Hangzhou (CN)

(72) Inventors: Riyong Liu, Hangzhou (CN); Zhiming Wang, Hangzhou (CN); Yunfeng He, Hangzhou (CN); Yu Wang, Hangzhou (CN); Zhicheng Fu, Hangzhou (CN); Tianwen Yan, Hangzhou (CN); Chunlan Hu, Hangzhou (CN); Guowei Su, Hangzhou (CN); Changcheng Tan, Hangzhou (CN); Xupeng Ding, Hangzhou (CN); Hui Yang, Hangzhou (CN); Hongying Wang, Hangzhou (CN); Qiong Ding, Hangzhou (CN); Qian Wang, Hangzhou (CN); Haiyan Wen, Hangzhou (CN); Kai Fan, Hangzhou (CN)

(73) Assignee: HANGZHOU GRAND BIOLOGIC PHARMACEUTICAL INC., Hangzhou (CN)

( * ) Notice: Subject to any disclaimer, the term of this patent is extended or adjusted under 35 U.S.C. 154(b) by 559 days.

(21) Appl. No.: 18/312,166

(22) Filed: May 4, 2023

(65) Prior Publication Data

US 2023/0346896 A1 Nov. 2, 2023

Related U.S. Application Data

(63) Continuation of application No. PCT/CN2021/129072, filed on Nov. 5, 2021.

(30) Foreign Application Priority Data

Nov. 5, 2020 (CN) ........................ 202011224610.1

(51) Int. Cl.
*A61K 38/44* (2006.01)
*A61K 47/02* (2006.01)
(Continued)

(52) U.S. Cl.
CPC .............. *A61K 38/44* (2013.01); *A61K 47/02* (2013.01); *A61K 47/10* (2013.01); *A61K 47/12* (2013.01)

(58) Field of Classification Search
CPC ...... A61K 38/44; A61K 47/12; C12N 9/0048; C12N 9/96; C12Y 107/03003; A61P 3/00
See application file for complete search history.

(56) References Cited

U.S. PATENT DOCUMENTS

| | | | | |
|---|---|---|---|---|
| 9,193,967 | B2 * | 11/2015 | Zhang | A61P 13/12 |
| 2009/0169534 | A1 | 7/2009 | Hartman | |
| 2019/0316097 | A1 * | 10/2019 | Hartman | A61K 47/60 |

FOREIGN PATENT DOCUMENTS

| | | |
|---|---|---|
| CN | 101302501 A | 11/2008 |
| CN | 101327327 A | 12/2008 |

(Continued)

OTHER PUBLICATIONS

U.S. Appl. No. 17/521,898 (Year: 2021).*

(Continued)

*Primary Examiner* — Ruth A Davis

(74) *Attorney, Agent, or Firm* — BOND, SCHOENECK & KING, PLLC; George R. McGuire

(57) ABSTRACT

Provided is a method for preparing a polyethylene glycol-modified urate oxidase, at least 11 of the following amino acid sites of the polyethylene glycol-modified urate oxidase have a PEG modification: $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$, and the preparation method includes: performing a coupling reaction between urate oxidase and (Continued)

polyethylene glycol, wherein the polyethylene glycol is provided in the form of an acidic solution, and a molar ratio of the urate oxidase to the polyethylene glycol is 1: (56 to 94), to obtain the polyethylene glycol-modified urate oxidase.

20 Claims, 12 Drawing Sheets

Specification includes a Sequence Listing.

(51) Int. Cl.

| | |
|---|---|
| ***A61K 47/10*** | (2017.01) |
| ***A61K 47/12*** | (2006.01) |

(56) References Cited

FOREIGN PATENT DOCUMENTS

| | | | |
|---|---|---|---|
| CN | 101928704 | A | 12/2010 |
| CN | 102051348 | A | 5/2011 |
| CN | 102634492 | A | 8/2012 |
| CN | 103756983 | A | 4/2014 |
| CN | 109682901 | A | 4/2019 |
| CN | 109963597 | A | 7/2019 |
| JP | 2008535499 | A | 9/2008 |
| JP | 2022531995 | A | 7/2022 |
| WO | 0007629 | A2 | 2/2000 |
| WO | 0007629 | A3 | 6/2000 |
| WO | 2020228618 | A1 | 11/2020 |
| WO | 2022228618 | A1 | 11/2022 |

OTHER PUBLICATIONS

U.S. Appl. No. 18/312,292 (Year: 2023).*

Result #1, SEQ ID No: 8, 100% match to claimed SEQ ID No. 1, U.S. Appl. No. 16/202,743, US 2019/0316097 (Year: 2026).*

Result #15, SEQ ID No: 3, 95.1% match to claimed SEQ ID No. 1, U.S. Appl. No. 13/985,273, U.S. Pat. No. 9,193,967 (Year: 2026).*

Translated Japanese Office Action, Application No. 2023-527076, dated Jun. 21, 2024, pp. 1-12.

Translated Chinese Second Office Action, App. No. 202011224613.5, dated Apr. 13, 2024, pp. 1-7.

"Urate oxidase preparations and their applications", Nonpatent Literature Transmittal Letter, Application No. 2023-527119, dated Apr. 26, 2020.

"Urate oxidase preparations and their applications", Statement on a nonproprietary name adopted by the USAN Council, Application No. 2023-527119, Dated Apr. 26, 2020, pp. 1-2.

AU Examination Report, Application No. 2021373176, Dated Dec. 6, 2024, Entire document.

EP Search Report, Application No. 21888666.1-1111 / 4241841 PCT/CN2021129072, Dated Oct. 22, 2024, Entire document.

Uenishi, H., et al. NP_999435.1: Genbank, Oct. 11, 2020.

International Search Report and Written Opinion of PCT/CN2021/129072.

Hui, Guo Yuantian, et. al., Effect of PEGylation on Properties of Uricase, Pharmaceutical Biotechnology, 2011, pp. 488-491, vol. 18—Iss. 6, China, CLC No. TQ320.67;Q55, A Article No. 1005-8915(2011)06-0488-04.

Zhang, Chun, et. al., Impact of Large Aggregated Uricases and PEG Diol on Accelerated Blood Clearance of PEGylated Canine Uricase, PLoS ONE, 2012, pp. 1-11, vol. 7—Iss. 6, www.plosone.org, e39659, DOI: 10.1371/journal.pone.0039659.

English translation of Chinese 1st Office Action & 1st Search, CN Application No. 202011224613.5, dated Jun. 7, 2023, entire document.

AU office action, Application No. 2021373176, dated Jul. 25, 2024, entire document.

Supplementary Partial EP Search Report, App. No. 21888666, dated Jul. 29, 2024, entire document.

Translated Chinese Notification to Grant Patent Right for Invention, Application No. 202011224610.1, dated Sep. 2, 2024, entire document.

* cited by examiner

METHOD FOR PREPARING POLYETHYLENE GLYCOL-MODIFIED URATE OXIDASE

CROSS-REFERENCE TO RELATED APPLICATIONS

This application is a by-pass continuation of International Application No. PCT/CN2021/129072, filed on Nov. 5, 2021, which claims priority to Chinese patent application No. 202011224610.1, filed on Nov. 5, 2020, the entire disclosures of which are incorporated herein by reference.

REFERENCES TO AN ELECTRONIC SEQUENCE LISTING

The contents of the electronic sequence listing of POI230612PUS-Sequence listing.xml; size 12 KB bytes; Date of Creation Apr. 19, 2023, is hereby incorporated by reference in its entirety.

TECHNICAL FIELD

The present disclosure relates to the field of biomedicine, in particular, the present disclosure relates to a method for preparing polyethylene glycol-modified urate oxidase, more particularly, the present disclosure relates to a method for preparing polyethylene glycol-modified urate oxidase, a method for reducing the immunogenicity of urate oxidase, polyethylene glycol-modified urate oxidase, pharmaceutical compositions, pharmaceutical uses of polyethylene glycol-modified urate oxidase.

BACKGROUND

Gout is a disease caused by the disorder of purine metabolism, with a clinical feature of hyperuricemia, and tophus is formed due to the deposition of urate under the skin, at joints, and in kidneys. The purine in the human body undergoes a series of changes, and the formed final product is uric acid. Hyperuricemia may occur when a concentration of uric acid in blood exceeds 70 mg/L. Among them, 5% to 12% of patients with hyperuricemia may progress to gout. Once a concentration of sodium urate in blood or synovial fluid reaches a saturated state, microcrystals of sodium urate salt can be formed, inducing gouty arthritis. Over time, chronic hyperuricemia may also cause the deposition of destructive crystalline uric acid deposits around joints, in soft tissues, and in certain organs, thereby inducing diseases such as acute gouty arthritis and chronic tophus arthritis, and joint deformities. Kidney damage is considered to be the second most common clinical manifestation of gout. The progressive nature of chronic hyperuricemia causes urate deposition in the medulla, renal tubules, and renal interstitium, stimulating the local area and causing inflammation, which is called chronic urate nephropathy. For patients with severe hyperuricemia (such as patients with certain malignant tumors, especially leukemia and lymphoma), a large amount of uric acid may be deposited in the renal collecting duct, renal pelvis, calyx and ureter in a short period of time, resulting in obstruction of lumen and anuresis and inducing acute renal failure (also known as uric acid nephropathy).

In recent decades, with the improvement of people's living quality and changes in diet and living habits, the intake of high-protein and high-purine foods has increased, and the number of gout patients has been increasing year by year. In Europe, the number of gout patients has approximately doubled in the past 20 years. The current incidence of hyperuricemia and gout in China has increased to about 2% to 3%. If the clinical symptoms of hyperuricemia do not appear, it is only needed to control the diet. When the clinical symptoms caused by hyperuricemia appear, drug treatment is required. Conventional clinical treatments currently include: analgesic and anti-inflammatory drugs, such as colchicine, ibuprofen, naproxen, etc., which are mainly used to control the symptoms of acute attacks of gouty arthritis, eliminating local pain, swelling and inflammation of the joints; uricosuric agents that promote the excretion of uric acid (ineffective if the kidney function is reduced), such as probenicid, sulfinpyrazone, benzbromarone, etc.; drugs that inhibit the synthesis of uric acid, such as allopurinol. Allopurinol is the main therapeutic drug for patients suffering from tophus gout, renal insufficiency, leukemia, and certain genetic diseases, and it can inhibit xanthine oxidase to disenable the conversion from hypoxanthine and xanthine into uric acid. Allopurinol can be gradually oxidized in vivo to produce oxipurinol, which is easily soluble in water and excreted with the urine. However, the patients with chronic gout and with the formed tophus can be hardly cured by either of these conventional treatments. In addition, after long-term use of the above-mentioned drugs, patients will inevitably experience complications such as leukopenia, impaired heart function, impaired liver and kidney function, stimulation to the gastrointestinal system, aplastic anemia leading to diabetes, or gout.

Human hyperuricemia is related to the mutation and inactivation of the uricase gene during the evolution process. The mutation introduces premature termination codons into the coding sequence of the human uricase gene (Wu X, Lee C opipramol, Muzny D M, Caskey C T. Proc Natl Acad Sci USA. 1989.86: 9412-9416.). Therefore, human beings themselves cannot synthesize active uricase, so that human purine catabolism is terminated at uric acid (Wu X, Muzny D M, Lee C, Caskey C T. J Mol Evol. 1992. 34: 78-84.). The active uricase in the liver peroxisomes of non-human primates and other mammals can convert the less soluble urate (about 11 mg/100 ml water) into the more soluble allantoin (about 147 mg/100 ml water), which can be excreted more effectively by the kidneys (Wortmann R L, Kelley W N. Kelley's textbook of rheumatology (6th). 2001: 1339-1376). In Europe and America, uricase (Uricozyme) prepared by *Aspergillus* flavus has been used in the treatment of severe hyperuricemia associated with tumor chemotherapy for more than 10 years (Zittoun R, Dauchy F, Teilaud C, Barthelemy M, Bouchard P. Ann Med Interne. 1978.127: 479-482.). The recombinant *Aspergillus flavus* uricase drug, ELITEK, developed by the Sanofi (France) and produced by fermentation of beer yeast, has been approved by the FDA in 2002 and used for the short-term treatment of severe hyperuricemia induced by tumor chemotherapy (Pui C H, Relling M V, Lascombes F, Harrison P L, Struxiano A et al. Leukemia. 1997.11: 1813-1816.). Meanwhile, it was proved that the infusion of ELITEK can also reduce the volume of tophus (Potaux L, Aparicio M, Maurel C, Ruedas M E, Mart in C L. Nouv PresseMed. 1975.4: 1109-1112.). The PEG-modified recombinant porcine uricase (Pegloticase), which was approved by the FDA in September 2010 and produced by Savient (USA), is used for the treatment of refractory gout, but it was invalid in clinical applications for 50% of patients due to its failure in solving the problem of immunogenicity.

Uricase (E C 1.7.3.3) is widely present in microorganisms (*Bacillus fastidious, Candida monocytogenes, Aspergillus flavus*), plants (soybeans, chickpeas), animals (pigs, cattle, dogs, baboons) (Suzuki K, Sakasegawa S, Misaki H, Sugiyama M. J Biosci Bioeng. 2004. 98: 153-158), and in the presence of oxygen, it can catalyze uric acid to oxidize allantoin to release carbon dioxide (Retailleau P, Colloc'h, Denis V, Francoise B. Acta Cryst D.2004.60: 453-462.).

The active uricase is a tetrameric protein, composed of the same subunits, and each subunit has a molecular weight of about 34 kD and is composed of 301 to 304 amino acids. The pH at the highest enzyme activity of uricase in each solution is 8.0 (Bayol A etal.Biophys Chem.1995.54: 229-235.). Among all the sources of uricase currently known, the uricase with the highest activity is from *Aspergillus flavus*, up to 27 IU/mg; and the second is from *Bacillus fastidious*, with an activity maintained at 13 IU/mg (Huang S H, Wu T K. Eur J Biochem. 2004. 271: 517-523.). In addition, the uricase derived from legumes only has an activity of 2 to 6 IU/mg; for the uricase derived from mammals, after recombinant expression, the activity of the uricase derived from pigs can reach 5 IU/mg, the activity of the uricase derived from baboons is only 1 IU/mg (Michael H, Susan J. K. 2006. U.S. Pat. No. 7,056,713B1), and the uricase derived from human beings is inactive.

For the application in human body, due to the high activity of microbial uricase and the low immunogenicity of mammalian uricase, the uricase derived from these two sources became a research focus in the current development and application of recombinant uricase. However, the homology between the uricase derived from *Aspergillus flavus* and the predicted human uricase is less than 40% (Lee C C, Wu X, Gibbs R A, Cook R G, Muzny D M, Caskey C T. Science.1988.239: 1288-1291.), the human body is prone to produce antibodies against the uricase, which results in a rapid weakening of the effect of *Aspergillus flavus* uricase and at the same time causes severe allergic reactions, and thus *Aspergillus flavus* uricase cannot be used for long-term treatment. The human uricase gene loses activity due to mutation and becomes a pseudogene.

Therefore, the technology for the treatment of hyperuricemia based on urate oxidase still needs further development and improvement.

SUMMARY

The present disclosure is based on the Applicant's findings and knowledge of the following facts and problems:

The active urate oxidase is a homotetrameric protein, one-third of the amino acids of which are strongly hydrophobic amino acids, and the tetrameric proteins may easily aggregate to form octamers and larger aggregates. Molecules with a molecular weight above 100 kDa can effectively induce the body to produce an immune response, the molecular weight of the unmodified polymer urate oxidase protein has already reached 140 kDa, and the polymer uricase with greater molecular weight will have higher immunogenicity. The human body is prone to produce antibodies against uricase, thereby rapidly weakening the efficacy thereof and causing severe allergic reactions, and thus the uricase is unsuitable for long-term treatment. It has been proven that through covalent modification of proteins with PEG, the protein immunogenicity can be reduced, the protein solubility can be increased, and the protein half-life can be prolonged.

Duke University and Savient conducted research on chimeric uricase derived from pigs and baboons (Michael H, Susan J. K. 2006. U.S. Pat. No. 7,056,713B1). In this research, ε-amino group of lysine residue of the urease derived from pig-like sources was modified with methoxy-containing polyethylene glycol having a molecular weight of 10 kDa (10 kDa-mPEG-NPC), the modified product is Pegloticase, and thus the goal of treating intractable gout in the human body has been initially achieved without significantly reducing enzyme activity. Applicant found that the above-mentioned research results cannot completely solve the immunogenicity problem caused by the drug. Clinical subjects have experienced the disappearance of the uricase efficacy after multiple injections, which, according to Applicant's speculations, may be related to the excessively great molecular weight of the Pegloticase protein (Pegloticase having a molecular weight of 540 kDa). Further, since pegloticase is not suitable for injection, but suitable for intravenous bolus injection, the subjects' compliance with long-term use is reduced, thereby severely limiting its clinical application. So far, there is no long-acting urate oxidase drug having lower immunogenicity and suitable for subcutaneous injection.

The present disclosure aims to at least solve one of the technical problems in the related art to a certain extent.

In a first aspect of the present disclosure, the present disclosure provides a method for preparing a polyethylene glycol-modified urate oxidase. According to an embodiment of the present disclosure, at least 11 of the following amino acid sites of the polyethylene glycol-modified urate oxidase have a PEG modification, $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$, and the method includes: performing a coupling reaction between urate oxidase and polyethylene glycol to obtain the polyethylene glycol-modified urate oxidase, wherein the polyethylene glycol is provided in a form of an acidic solution, and a molar ratio of the urate oxidase to polyethylene glycol is 1: (56 to 94). The polyethylene glycol-modified urate oxidase prepared according to the method of the embodiments of the present disclosure has the PEG modification at at least 11 of the modification sites $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$. It should be noted that "urate oxidase" prepared in the present application should be understood in a broad sense, and refers to a generic name for a mixture of urate oxidases produced in the same batch in actual production practice. The polyethylene glycol-modified urate oxidase obtained according to the method of the embodiments of the present disclosure can greatly improve the in vivo stability of urate oxidase and reduce immunogenicity while guaranteeing the maximum enzyme activity, and has an in vivo efficacy after intramuscular injection equivalent to an in vivo efficacy after intravenous injection of an original patented drug.

According to an embodiment of the present disclosure, the method described above further includes at least one of the following additional technical features:

According to an embodiment of the present disclosure, the polyethylene glycol is provided in the form of an acidic solution. The inventors found that by dissolving PEG in an acidic solution, the hydrolysis of activated groups of polyethylene glycol before the reaction with the protein can be prevented, the effective activation efficiency of polyethylene glycol can be therefore effectively ensured, and moreover, the defects, such as excessively high local concentration, uneven dissolution, uneven contact between polyethylene glycol and the coupled protein, and the generation of bubbles interfering with the coupling reaction, etc., occurring when a polyethylene glycol solid is directly dissolved in the coupling reaction buffer, can be solved, thus effectively improving the efficiency of the coupling reaction between urate oxidase and polyethylene glycol.

According to an embodiment of the present disclosure, the acidic solution contains at least one selected from the group consisting of organic acids and inorganic acids.

According to an embodiment of the present disclosure, the organic acids are selected from acetic acid, oxalic acid, maleic acid, tartaric acid, citric acid, succinic acid, malonic acid, adipic acid, ascorbic acid, benzenesulfonic acid, benzoic acid, butyric acid, cyclopentylpropionic acid, digluconic acid, dodecylsulfuric acid, ethanesulfonic acid, formic acid, fumaric acid, glucoheptonic acid, glycerophosphoric acid, gluconic acid, heptanoic acid, hexanoic acid, 2-hydroxyethanesulfonic acid, digalacturonic acid, lactic acid, lauric acid, laurylsulfuric acid, malic acid, malonic acid, methanesulfonic acid, 2-naphthalenesulfonic acid, nicotinic acid, oleic acid, palmitic acid, pectic acid, 3-phenylpropionate, picrate, pivalic acid, propionic acid, stearic acid, p-toluenesulfonic acid, undecanoic acid, or pentanoic acid.

According to an embodiment of the present disclosure, the inorganic acids are selected from hydrochloric acid, hydrobromic acid, phosphoric acid, sulfuric acid, perchloric acid, hydriodic acid, nitric acid, persulfuric acid, boric acid, dichromic acid, silicic acid, chromic acid, or thiocyanic acid.

According to an embodiment of the present disclosure, a concentration of hydrogen ions in the acidic solution ranges from 1 mmol/L to 5 mmol/L.

According to an embodiment of the invention, the acidic solution contains hydrochloric acid, sulfuric acid, or glacial acetic acid.

According to an embodiment of the present disclosure, a concentration of the acid in the acidic solution ranges from 1 mmol/L to 5 mmol/L.

According to an embodiment of the present disclosure, the molar ratio of the urate oxidase to the polyethylene glycol is 1: (45 to 110).

According to an embodiment of the present disclosure, the molar ratio of the urate oxidase to the polyethylene glycol is 1: (56 to 94).

According to an embodiment of the present disclosure, a concentration of the polyethylene glycol in the acidic solution ranges from 100 mmol/L to 300 mmol/L. The present inventors found that when the concentration of polyethylene glycol in the acid is within the above concentration range, the viscosity of the reaction solution is appropriate, which is advantageous in improving the reaction efficiency and expanding industrial production.

According to an embodiment of the present disclosure, the polyethylene glycol has a molecular weight of not more than 6 KD. The inventors have found that by using polyethylene glycol with a molecular weight of not more than 6 KD to perform a coupling reaction with urate oxidase, the long-term activity of the obtained polyethylene glycol-modified urate oxidase in vivo is further enhanced, no anti-uricase antibody is generated, and almost no anti-PEG antibody is generated, i.e., the immunogenicity is further reduced.

According to an embodiment of the present disclosure, the polyethylene glycol has a monomethoxy group or a hydroxyl group.

According to an embodiment of the present disclosure, the polyethylene glycol is of a linear or branched structure.

According to an embodiment of the present disclosure, the polyethylene glycol is coupled to the urate oxidase via an amide bond.

According to an embodiment of the invention, the polyethylene glycol is a modifying polyethylene glycol, and a modification group of the modifying polyethylene glycol is selected from the group consisting of N-hydroxysuccinimide, N-hydroxysuccinimidyl carbonate, N-hydroxysuccinimidyl acetate, N-hydroxysuccinimidyl propionate, N-hydroxysuccinimidyl butyrate, N-hydroxysuccinimidyl succinate, and bis(p-nitrophenyl) carbonate.

According to an embodiment of the present disclosure, the modification group of the modified polyethylene glycol is N-hydroxysuccinimide.

According to an embodiment of the present disclosure, the coupling reaction is performed in a carbonate buffer solution.

According to an embodiment of the invention, the carbonate buffer solution has a pH of 9 to 11. The inventors found that when the buffer pH was lower than 9.0, the solubility of uricase would be seriously affected, and the next modification reaction could not be carried out, while when the buffer pH was higher than 11, the activity of uricase would be seriously affected, and the coupling efficiency of polyethylene glycol and urate oxidase would be reduced.

According to an embodiment of the present disclosure, a concentration of the urate oxidase in a coupling reaction system is 10 mg/ml. The inventors found that when the concentration of urate oxidase in the coupling reaction system is within the above-mentioned concentration, the viscosity of the reaction solution is appropriate, which is beneficial to improve the reaction efficiency and expand industrial production. Meanwhile, the inventors found that the protein concentration of urate oxidase affects the average degree of modification of urate oxidase, and under the condition that the obtained urate oxidase has the same average degree of modification of PEG, the feed ratio of PEG required by 10 mg/ml of urate oxidase is lower, thus saving production costs.

According to an embodiment of the present disclosure, the coupling reaction is performed at 5° C. to 30° C. for at least 60 min. The coupling reaction performed at the above-mentioned temperature conditions for at least 60 min is effective to achieve PEG modification at least 11 sites of $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$ of urate oxidase.

According to an embodiment of the present disclosure, the method further includes performing an ultrafiltration and/or purification treatment on a product of the coupling reaction. In turn, unmodified polyethylene glycol and by-products, such as NHS, can be effectively removed, effectively increasing the purity of the polyethylene glycol-modified urate oxidase obtained.

According to an embodiment of the present disclosure, at least one of the following four amino acid sites has the PEG modification: $K^{30}$, $K^{35}$, $K^{222}$, and $K^{231}$.

According to an embodiment of the present disclosure, the amino acid sites are positioned with the amino acid sequence set forth as SEQ ID NO: 1.

```
                                        (SEQ ID NO: 1)
TYKKNDEVEFVRTGYGKDMIKVLHIQRDGKYHSIKEVATTVQLTLSSKKD

YLHGDNSDVIPTDTIKNTVNVLAKFKGIKSIETFAVTICEHFLSSFKHVI

RAQVYVEEVPWKRFEKNGVKHVHAFIYTPTGTHFCEVEQIRNGPPVIHSG

IKDLKVLKTTQSGFEGFIKDQFTTLPEVKDRCFATQVYCKWRYHQGRDVD

FEATWDTVRSIVLQKFAGPYDKGEYSPSVQKTLYDIQVLTLGQVPEIEDM

EISLPNIHYLNIDMSKMGLINKEEVLLPLDNPYGKITGTVKRKLSSRL.
```

According to an embodiment of the present disclosure, the urate oxidase has an amino acid sequence set forth as any one of SEQ ID NOs: 1 to 7.

(SEQ ID NO: 2)
```
MAHYRNDYKKNDEVEFVRTGYGKDMIKVLHIQRDGKYHSIKEVATSVQLT
LSSKKDYLHGDNSDVIPTDTIKNTVNVLAKFKGIKSIETFAVTICEHFLS
SFKHVIRAQVYVEEVPWKRFEKNGVKHVHAFIYTPTGTHFCEVEQIRNGP
PVIHSGIKDLKVLKTTQSGFEGFIKDQFTTLPEVKDRCFATQVYCKWRYH
QGRDVDFEATWDTVRSIVLQKFAGPYDKGEYSPSVQKTLYDIQVLTLGQV
PEIEDMEISLPNIHYLNIDMSKMGLINKEEVLLPLDNPYGRITGTVKRKL
TSRL.
```

(SEQ ID NO: 3)
```
MYKNDEVEFVRTGYGKDMVKVLHIQRDGKYHSIKEVATSVQLTLSSKKDY
VYGDNSDIIPTDTIKNTVHVLAKFKGIKSIETFAMNICEHFLSSFNHVIR
AQVYVEEVPWKRFEKNGVKHVHAFIHNPTGTHFCEVEQMRSGPPVIHSGI
KDLKVLKTTQSGFEGFIKDQFTTLPEVKDRCFATKVYCKWRYHQGRDVDF
EATWDTVRDIVLEKFAGPYDKGEYSPSVQKTLYDIQVHSLSRVPEMEDME
ISLPNIHYFNIDMSKMGLINKEEVLLPLDNPYGKITGTVKRKLSSRL.
```

(SEQ ID NO: 4)
```
MAHYHNDYKKNDEVEFVRTGYGKDMVKVLHIQRDGKYHSIKEVATSVQLT
LSSKKDYVYGDNSDIIPTDTIKNTVHVLAKFKGIKSIETFAMNICEHFLS
SFNHVIRAQVYVEEVPWKRFEKNGVKHVHAFIHNPTGTHFCEVEQMRSGP
PVIHSGIKDLKVLKTTQSGFEGFIKDQFTTLPEVKDRCFATKVYCKWRYH
QGRDVDFEATWDTVRDIVLEKFAGPYDKGEYSPSVQKTLYDIQVHSLSRV
PEMEDMEISLPNIHYFNIDMSKMGLINKEEVLLPLDNPYGRITGTAKRKL
ASKL.
```

(SEQ ID NO: 5)
```
MAHYHNDYQKNDEVEFVRTGYGKDMVKVLHIQRDGKYHSIKEVATSVQLT
LNSRREYLHGDNSDIIPTDTIKNTVQVLAKFKGIKSIETFAMNICEHFLS
SFNHVIRVQVYVEEVPWKRFEKNGVKHVHAFIHTPTGTHFCEVEQLRSGP
PVIHSGIKDLKVLKTTQSGFEGFLKDQFTTLPEVKDRCFATQVYCKWRYH
QGRDVDFEATWEAVRGIVLKKFAGPYDKGEYSPSVQKTLYDIQVLSLSQL
PEIEDMEISLPNIHYFNIDMSKMGLINKEEVLLPLDNPYGRITGTVKRKL
TSRL.
```

(SEQ ID NO: 6)
```
MAHYHNDYKKNDEVEFVRTGYGKDMVKVLHIQRDGKYHSIKEVATSVQLT
LSSKKDYLHGDNSDIIPTDTIKNTVHALAKFKGIKSIEAFAVNICQHFLS
SFNHVIRTQVYVEEIPWKRLEKNGVKHVHAFIHTPTGTHFCEVEQLRSGP
PVIHSGIKDLKVLKTTQSGFEGFIKDQFTTLPEVKDRCFAAQVYCKWRYH
QCRDVDFEATWDTIRDVVLEKFAGPYDKGEYSPSVQKTLYDIQVVSLSQV
PEIDDMEISLPNIHYFNIDMSKMGLINKEEVLLPLDNPYGKITGTVKRKL
SSRL.
```

-continued (SEQ ID NO: 7)
```
MADYHNNYKKNDELEFVRTGYGKDMVKVLHIQRDGKYHSIKEVATSVQLT
TLSSKKDYLHGDNSDIIPTDTIKNTVHVLAKFKGIKSIEAFGVNICEYFL
SSFNHVIRAQVYVEEIPWKRLEKNGVKHVHAFIHTPTGTHFCEVEQLRSG
PPVIHSGIKDLKVLKTTQSGFEGFIKDQFTTLPEVKDRCFATQVYCKWRY
HQCRDVDFEATWGTIRDLVLEKFAGPYDKGEYSPSVQKTLYDIQVLSLSR
VPEIEDMEISLPNIHYFNIDMSKMGLINKEEVLLPLDNPYGKITGTVKRK
LSSRL.
```

The amino acid sequence set forth as SEQ ID NO: 1 is an amino acid sequence of a chimeric uricase (pig-baboon) derived from pig and baboon; the amino acid sequence set forth as SEQ ID NO: 2 is an amino acid sequence of pig-derived urate oxidase; the amino acid sequence set forth as SEQ ID NO: 3 is an amino acid sequence of a chimeric urate oxidase (canine-baboon) derived from canine and baboon; the amino acid sequence set forth as SEQ ID NO: 4 is an amino acid sequence of canine-derived urate oxidase; the amino acid sequence set forth as SEQ ID NO: 5 is an amino acid sequence of bovine-derived urate oxidase; the amino acid sequence set forth as SEQ ID NO: 6 is an amino acid sequence of monkey-derived urate oxidase; and the amino acid sequence set forth as SEQ ID NO: 7 is an amino acid sequence of baboon-derived urate oxidase.

It should be noted that lysine in the present disclosure is positioned based on the amino acid sequence set forth as SEQ ID NO: 1. For example, $K^4$ refers to the lysine located at position 4 based on the amino acid sequence set forth as SEQ ID NO: 1. The uricase has the amino acid sequence set forth as any one of SEQ ID NOs: 1 to 7, the polypeptide having at least 70%, at least 75%, at least 80%, at least 85%, at least 90%, at least 95%, or at least 99% identity with any one of SEQ ID NOs: 1 to 7, and the polypeptide having the amino acid sequence set forth as any one of SEQ ID NOs: 1 to 7 in which one or more amino acids are substituted, deleted and/or added have homology in their structures. Those skilled in the art, through sequence mapping, can determine respective positions corresponding to $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$ on any one of SEQ ID NOs: 2 to 7, or the polypeptide having at least 70%, at least 75%, at least 80%, at least 85%, at least 90%, at least 95%, or at least 99% identity with any one of SEQ ID NOs: 1 to 7, or the polypeptide having the amino acid sequence set forth as any one of SEQ ID NOs: 1 to 7 in which one or more amino acids are substituted, deleted and/or added, and then allow the PEG modification to occur at the corresponding positions on the above-mentioned polypeptide sequence, thereby achieving the advantages of the polyethylene glycol-modified urate oxidase of the present disclosure, such as low immunogenicity, high stability in vivo, and applicability for intramuscular injection.

For example, according to the embodiments of the present disclosure, sites of the sequence set forth as SEQ ID NO: 2 corresponding to sites $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$ of the sequence set forth as SEQ ID NO: 1 include $M^1$, $K^9$, $K^{10}$, $K^{36}$, $K^{41}$, $K^{82}$, $K^{85}$, $K^{103}$, $K^{118}$, $K^{122}$, $K^{126}$, $K^{158}$, $K^{185}$, $K^{228}$, $K^{237}$, $K^{272}$, $K^{278}$, $K^{297}$, and $K^{299}$; sites of the sequence set forth as SEQ ID NO: 3 corresponding to the above-mentioned respective sites of the sequence set forth as SEQ ID NO: 1 include $M^1$, $K^3$, $K^{29}$, $K^{34}$, $K^{75}$, $K^{78}$, $K^{111}$, $K^{115}$, $K^{119}$, $K^{151}$, $K^{178}$, $K^{221}$, $K^{230}$, $K^{265}$, $K^{271}$, $K^{284}$, $K^{290}$, and $K^{292}$; sites of the sequence set forth as SEQ ID NO: 4 corresponding to the above-mentioned respective sites of the sequence set forth as SEQ ID NO: 1 include $M^1$, $K^9$, $K^{10}$, $K^{36}$, $K^{41}$, $K^{82}$, $K^{85}$, $K^{118}$, $K^{122}$, $K^{126}$, $K^{158}$, $K^{185}$, $K^{228}$, $K^{237}$, $K^{272}$, $K^{278}$, $K^{297}$, and $K^{299}$; sites of the sequence set forth as SEQ ID NO: 5 corresponding to the above-mentioned respective sites of the sequence set forth as SEQ ID NO: 1 include $M^1$, $K^{10}$, $K^{36}$, $K^{41}$, $K^{82}$, $K^{85}$, $K^{118}$, $K^{122}$, $K^{126}$, $K^{158}$, $K^{185}$, $K^{228}$, $K^{237}$, $K^{272}$, $K^{278}$, $K^{297}$, and $K^{299}$; sites of the sequence set forth as SEQ ID NO: 6 corresponding to the above-mentioned respective sites of the sequence set forth as SEQ ID NO: 1 include $M^1$, $K^9$, $K^{10}$, $K^{36}$, $K^{41}$, $K^{82}$, $K^{85}$, $K^{118}$, $K^{122}$, $K^{126}$, $K^{158}$, $K^{185}$, $K^{228}$, $K^{237}$, $K^{272}$, $K^{278}$, $K^{291}$, $K^{297}$, and $K^{299}$; sites of the sequence set forth as SEQ ID NO: 7 corresponding to the above-mentioned respective sites of the sequence set forth as SEQ ID NO: 1 include $M^1$, $K^9$, $K^{10}$, $K^{36}$, $K^{41}$, $K^{82}$, $K^{85}$, $K^{118}$, $K^{122}$, $K^{126}$, $K^{158}$, $K^{185}$, $K^{228}$, $K^{237}$, $K^{272}$, $K^{278}$, $K^{291}$, $K^{2976}$, and $K^{299}$. Applicant found through experiments that, after at least 11 sites of the respective sites of the amino acid sequence set forth as any one of SEQ ID NOs: 2 to 7 are modified with PEG, the obtained PEG-modified urate oxidase has low immunogenicity, high stability in vivo, and applicability for intramuscular injection.

According to an embodiment of the present disclosure, peak areas of at least 11 predetermined peptide fragments in a peptide map of the polyethylene glycol-modified urate oxidase are reduced by a relative proportion of 75% or more, preferably 80% or more, more preferably 90% or more, compared with urate oxidase unmodified with polyethylene glycol. The polyethylene glycol-modified urate oxidase according to the embodiment of the present disclosure has the advantages of low immunogenicity, high stability in vivo, and applicability for intramuscular injection.

According to an embodiment of the present disclosure, the peptide map of the polyethylene glycol-modified urate oxidase has peptide fragments with peak area reduction shown in Table 8.

According to an embodiment of the present disclosure, the peptide map of the polyethylene glycol-modified urate oxidase is shown in FIG. 6 or FIG. 7.

In a second aspect of the invention, the present disclosure provides a method of reducing the immunogenicity of urate oxidase. According to an embodiment of the present disclosure, at least 11 of the following amino acid sites of the polyethylene glycol-modified urate oxidase has a PEG modification, $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$ and $K^{293}$, and the method includes: performing a coupling reaction between urate oxidase and polyethylene glycol, wherein the polyethylene glycol is provided in the form of an acidic solution, and a molar ratio of the urate oxidase to the polyethylene glycol is 1: (56 to 94). According to the method of the embodiment of the present disclosure, the immunogenicity of urate oxidase can be effectively reduced, and the resulting urate oxidase has higher in vivo safety and a better long-lasting effect.

It can be understood that the additional technical features of the above-mentioned method for preparing polyethylene glycol-modified urate oxidase and the technical effects possessed by the additional technical features are applicable to the additional technical features of the method for reducing the immunogenicity of urate oxidase according to the embodiments of the present disclosure, and the additional technical features of the method for reducing the immunogenicity of urate oxidase according to the embodiments of the present disclosure will not be described in detail herein.

In a third aspect of the invention, the present disclosure provides a polyethylene glycol-modified urate oxidase. According to an embodiment of the present disclosure, the glycol-modified urate oxidase is obtained by the method described above. The polyethylene glycol-modified urate oxidase according to the embodiments of the present disclosure can greatly improve the in vivo stability of urate oxidase and reduce immunogenicity while guaranteeing the maximum enzyme activity, and has an in vivo efficacy after intramuscular injection equivalent to an in vivo efficacy after intravenous injection of an analogous drug on the market.

In a fourth aspect of the present disclosure, a pharmaceutical composition is provided. According to an embodiment of the present disclosure, the pharmaceutical composition includes the urate oxidase described above. The pharmaceutical composition according to the embodiment of the present disclosure has the advantages of low immunogenicity, high in vivo stability, applicability for intramuscular injection, and can be used for the treatment or prevention of hyperuric acid-related diseases.

According to an embodiment of the present disclosure, the pharmaceutical composition further includes at least one of the following additional technical features:

According to an embodiment of the present disclosure, the pharmaceutical composition further includes a pharmaceutically acceptable adjuvant.

According to an embodiment of the present disclosure, the pharmaceutical composition further includes additional drugs for treating or preventing hyperuric acid-related diseases.

In a fifth aspect, the present disclosure provides the use of the urate oxidase described above or the pharmaceutical composition described above in the manufacture of a medicament for the treatment of hyperuric acid-related diseases and reducing a uric acid level in a biological fluid of a subject in need thereof. The urate oxidase according to embodiments of the present disclosure has the advantages of low immunogenicity, high in vivo stability, and applicability for intramuscular injection, and has significant advantages in the treatment of the hyperuric acid-related diseases.

According to an embodiment of the present disclosure, the use described above further comprises at least one of the following additional technical features:

According to an embodiment of the present disclosure, the hyperuric acid-related diseases include chronic hyperuricemia, gout, kidney disease, hyperuricemic arthritis, renal calculi, tophus, hypertension, diabetes, hypertriglyceridemia, metabolic syndrome, and coronary heart disease.

According to an embodiment of the invention, the biological fluid is urine or blood.

DESCRIPTION OF EMBODIMENTS

Figure 1:
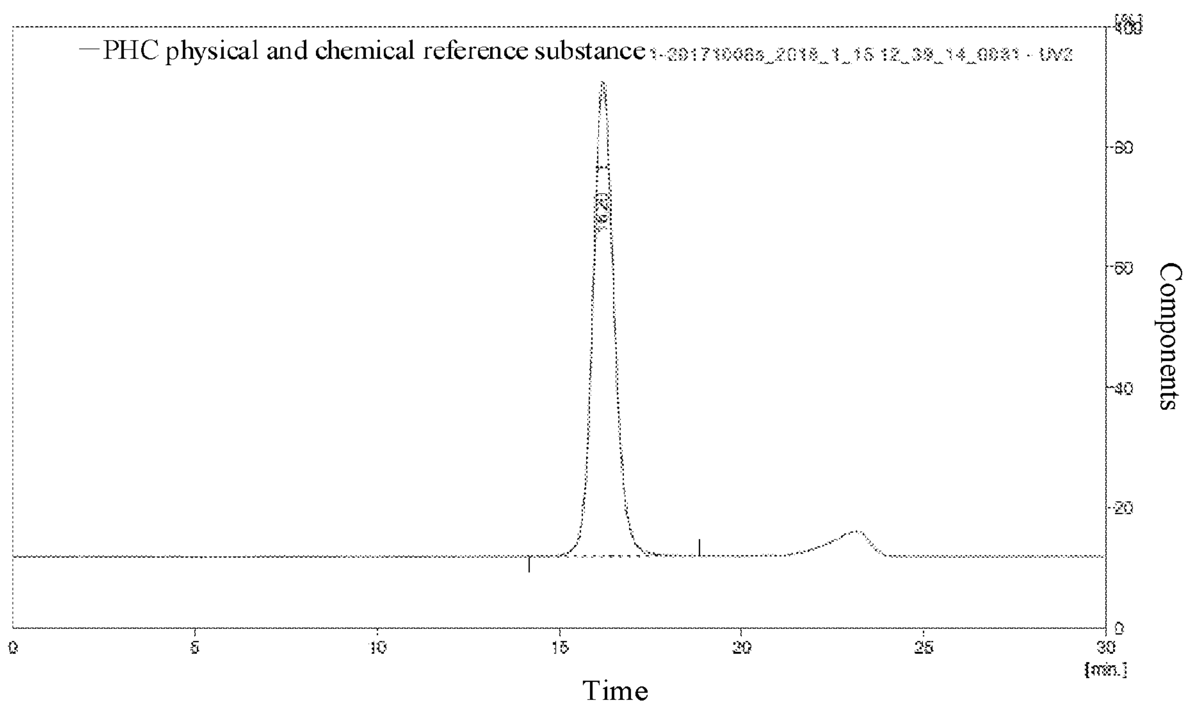
FIG. 1 is a spectrum of SEC-HPLC-UV detection of a PHC physical and chemical reference substance according to an embodiment of the present disclosure.
Figure 2:
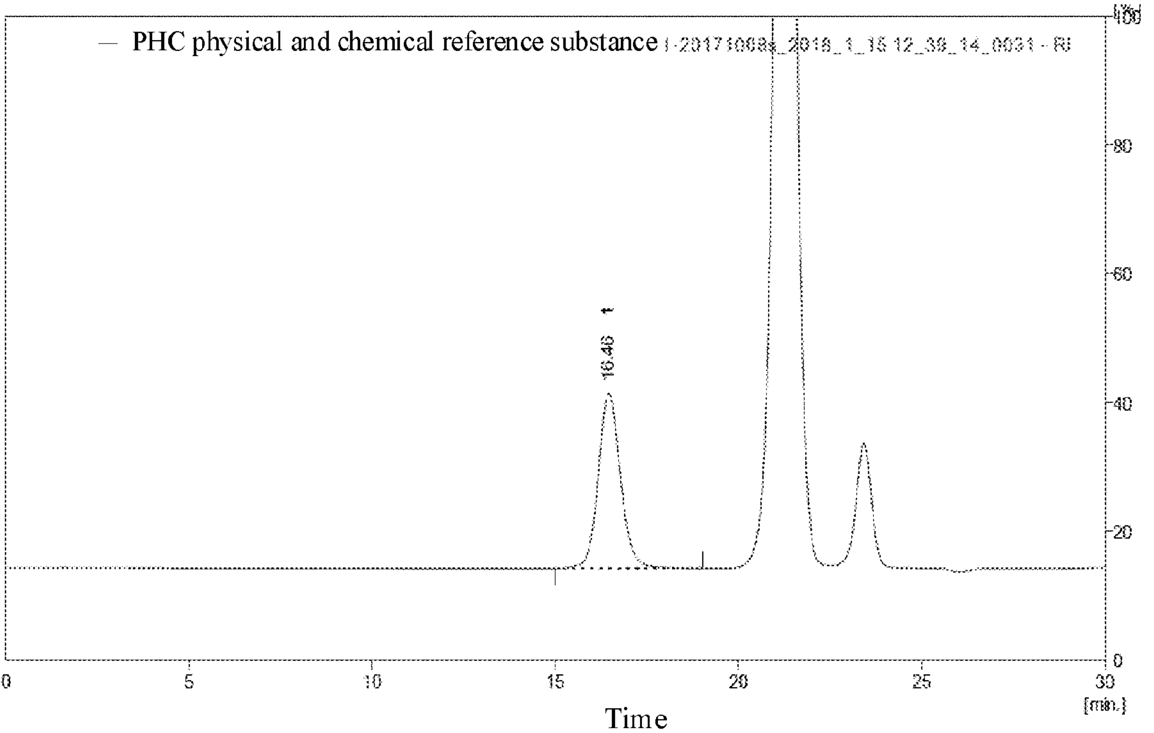
FIG. 2 is a spectrum of SEC-HPLC-RI detection of a PHC physical and chemical reference substance according to an embodiment of the present disclosure.
Figure 3:
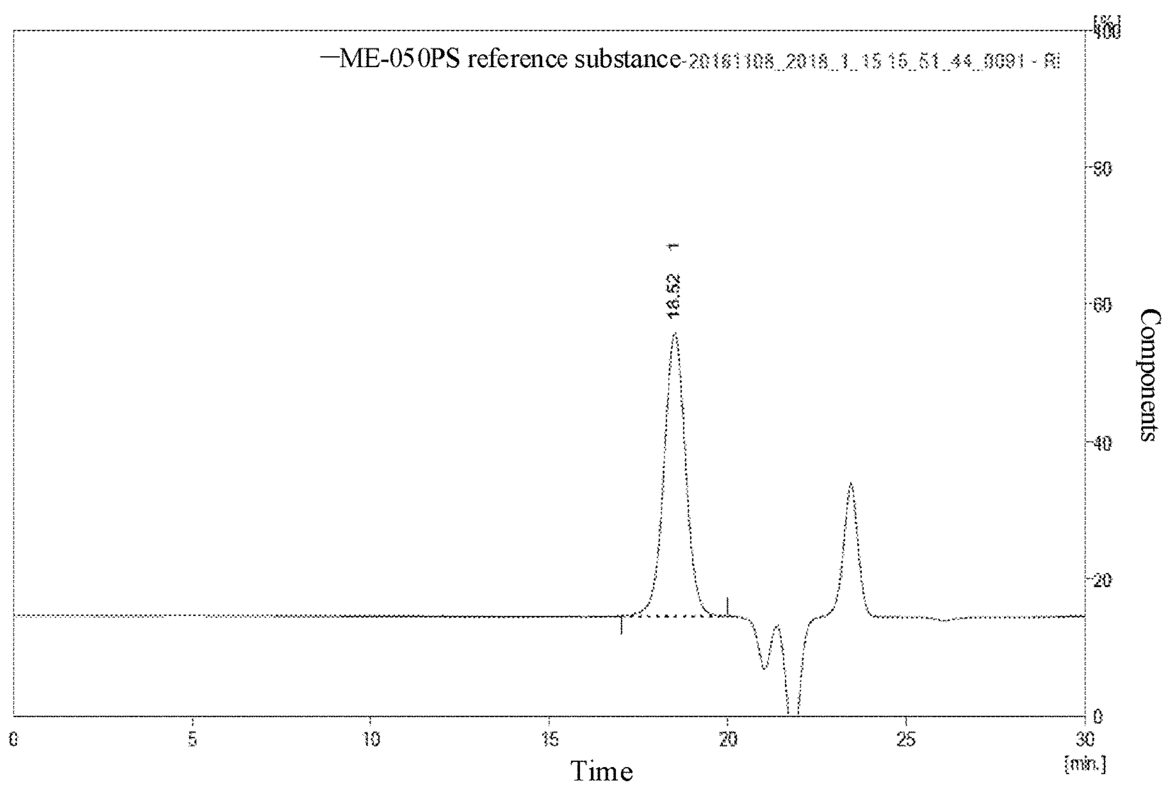
FIG. 3 is a spectrum of SEC-HPLC-RI detection of a PEG reference substance according to an embodiment of the present disclosure.
Figure 4:
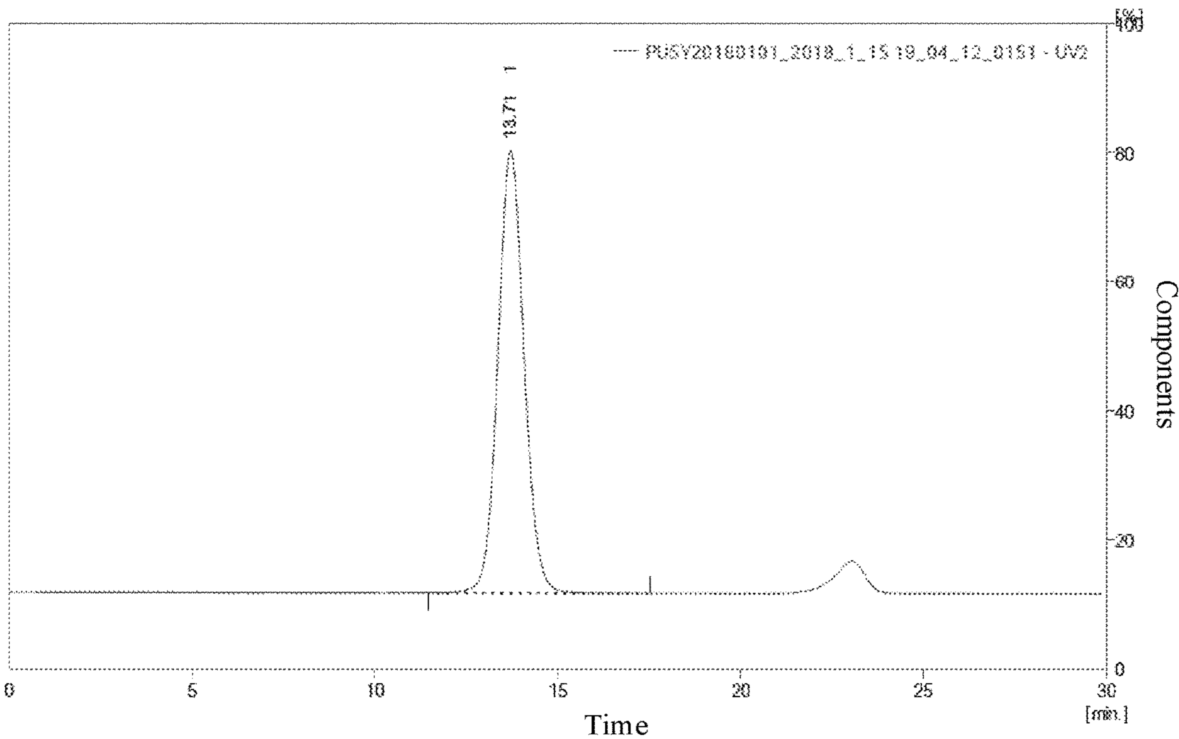
FIG. 4 is a spectrum of SEC-HPLC-UV detection of a PU5 modification product according to an embodiment of the present disclosure.
Figure 5:
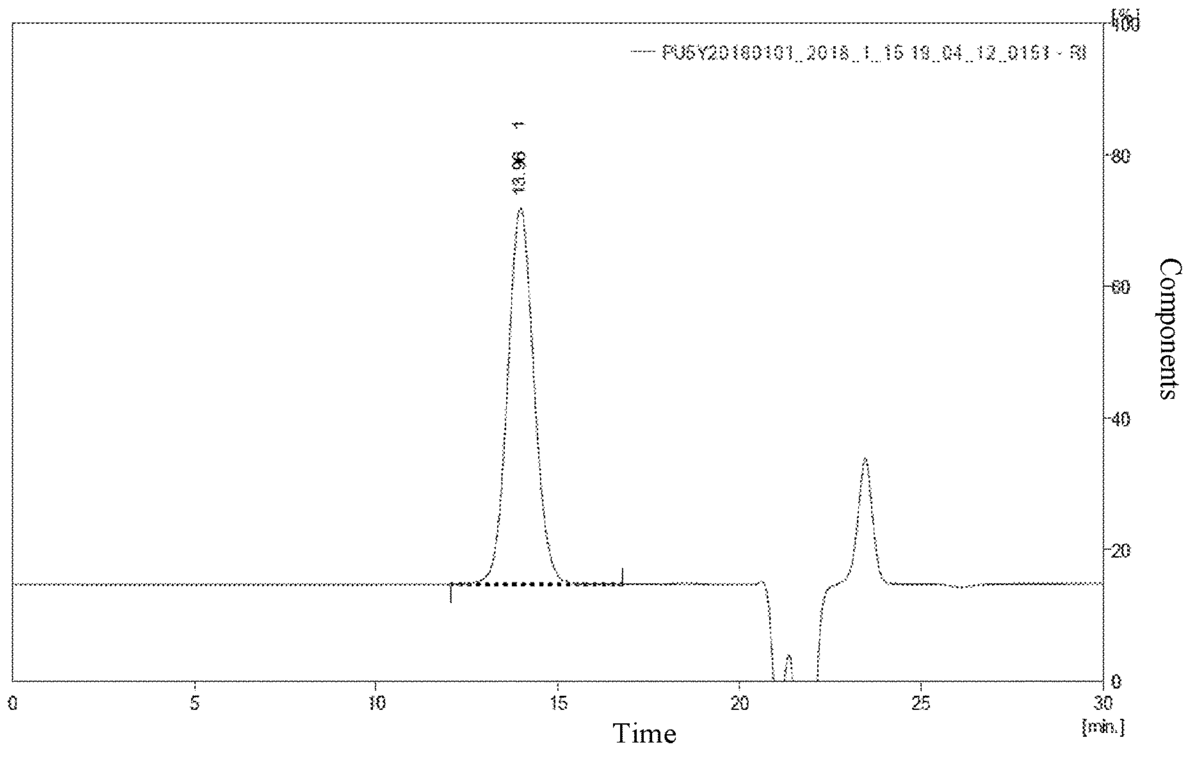
FIG. 5 is a spectrum of SEC-HPLC-RI detection of a PU5 modification product according to an embodiment of the present disclosure.

The embodiments of the present disclosure are described in detail below, and examples of the embodiments are illustrated in the accompanying drawings. The embodiments described below with reference to the accompanying drawings are illustrative and are intended to explain the present disclosure, but should not be understood as a limitation of the present disclosure.

An object of the present disclosure is to provide a method for preparing a polyethylene glycol-modified urate oxidase.

Another object of the present disclosure is to provide a novel polyethylene glycol-modified urate oxidase.

Another object of the present disclosure is to provide a method for effectively reducing the immunogenicity of urate oxidase, which can effectively reduce the immunogenicity of urate oxidase and improve the safety and stability of urate oxidase in vivo.

Another object of the present disclosure is to provide the use of the polyethylene glycol-urate oxidase conjugate obtained as above, which can achieve a long-lasting efficacy in vivo and significantly reduce the serum uric acid level, and can be used for the treatment of hyperuricemia and gout.

As used herein, the terms "urate oxidase" and "uricase" are interchangeable, and they both refer to a class of enzymes described in the present disclosure that can catalyze the oxidation of uric acid to produce allantoin and hydrogen peroxide. The terms "urate oxidase analogue", "uricase analogue", and "uricase derivative" are interchangeable, and they all refer to that parts of amino acids of a protein structural sequence of urate oxidase can be subjected to a structural modification such as substitution, deletion, or addition under the premise that the activity of urate oxidase for specifically catalyzing the conversion of uric acid into allantoin and hydrogen peroxide is maintained, thereby achieving the advantages of the present disclosure, including but not limited to reducing immunogenicity, increasing protein stability, and facilitating further polyethylene glycol modification.

Urate oxidase is not particularly limited, and can be urate oxidase and urate oxidase analogues derived from any source. Representative examples include, but are not limited to, mammalian sources, microorganisms, plants, etc.

In another preferred embodiment, the urate oxidase and urate oxidase analogues thereof are derived from mammals, preferably, the amino acid sequence set forth as any one of SEQ ID NO: 1, SEQ ID NO: 2, SEQ ID NO: 3, and SEQ ID NO: 4, and more preferably, the amino acid sequence set forth as SEQ ID NO: 1.

The urate oxidase derived from different species according to the present disclosure can be obtained through various manners, including but not limited to natural extraction, chemical synthesis, genetic engineering recombinant expression, etc.

In another preferred embodiment, through recombinant technology of urate oxidase, a coding sequence of the urate oxidase protein sequence (SEQ ID NO: 1) is subjected to recombinant expression in a host cell.

In another preferred embodiment, the urate oxidase is prepared and obtained in a manner that *E. coli* or yeast is used as a host to construct a recombinant expression strain, and *E. coli* is more preferably used as host bacteria for recombinant expression.

As used herein, the polyethylene glycol-modified urate oxidase described in the present disclosure is obtained by covalently modifying urate oxidase with polyethylene glycol. The polyethylene glycol (PEG) refers to a mixture of ethylene oxide condensation polymer and water, represented by a general formula $H(OCH_2CH_2)_nOH$, which is a hydrophilic and linear or branched polymer with neutral pH and high water solubility and without toxicity. Due to the non-toxicity and good biocompatibility of PEG, the FDA has approved a variety of PEG-modified recombinant protein drugs on the market, proving that PEG can be used to reduce the immunogenicity of the protein, increase the solubility of the protein, and extend the half-life of the protein. In order to bind PEG to protein, one or more ends of PEG need to be activated, and the activation can be performed by selecting the corresponding modification groups according to the groups on the target protein to be modified, such as amino, sulfhydryl, carboxyl or hydroxyl.

In another preferred embodiment, a site of urate oxidase and uricase analogues for PEG modification according to the present disclosure is an ε-amino group of lysine residues, or an α-amino group of a small amount of N-terminal lysine residues. The urate oxidase is covalently connected to the modification group of PEG through a urethane bond, a secondary amino bond, or an amide bond. Preferably, a polyethylene glycol molecule is coupled with urate oxidase to form an amide bond. The modification groups of polyethylene glycol include, but are not limited to, N-hydroxysuccinimides, including but not limited to N-hydroxysuccinimide (NHS), N-hydroxysuccinimidyl carbonate (SC), N-hydroxysuccinimidyl acetate (SCM), N-hydroxysuccinimidyl propionate (SPA), N-hydroxysuccinimidyl butyrate (SBA), N-hydroxysuccinimidyl succinate (SS), etc. The blocking group of polyethylene glycol includes, but is not limited to, monomethoxy, ethoxy, glucose, or galactose, preferably monomethoxy.

In another preferred embodiment, the polyethylene glycol may be linear or linear.

In another preferred embodiment, a relative molecular weight of the used polyethylene glycol for polyethylene glycol-modified urate oxidase is not more than 6 KD, preferably 1 KD to 5 KD, and most preferably 5 KD. It should be noted that the "relative molecular weight of polyethylene glycol" mentioned herein refers to a relative molecular weight of polyethylene glycol without modification groups, which has a general meaning in the related art. PEG, after the activation by the active groups, has a total relative molecular weight slightly greater than 5 KD, for example, in a range of 5 KD+10%.

In another preferred embodiment, the polyethylene glycol-modified urate oxidase has the following characteristics:

(1) At least 11 of the following amino acid sites in the urate oxidase have a PEG modification: $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$.

(2) One urate oxidase molecule is coupled with 11 to 13 polyethylene glycol molecules on average.

(3) $K^{30}$ and/or $K^{35}$, as well as $K^{222}$ and/or $K^{231}$ contained in the urate oxidase sequence set forth as SEQ ID NO: 1 are modified and coupled with polyethylene glycol; and (4) The polyethylene glycol-modified urate oxidase has lower immunogenicity in vivo.

In another aspect of the present disclosure, a method for effectively reducing immunogenicity of urate oxidase is provided. This technology can effectively reduce the immunogenicity of urate oxidase and improve the in vivo stability of urate oxidase.

As used herein, the polyethylene glycol-modified urate oxidase is characterized in that, the urate oxidase is not particularly limited, and can be urate oxidase and urate oxidase analogues derived from any source, representative examples of which include, but are not limited to, sources of mammals, microorganisms, plants, etc.

In another preferred embodiment, the urate oxidase and the urate oxidase analogues are derived from mammals. The amino acid sequences of SEQ ID NO: 1, SEQ ID NO: 2, SEQ ID NO: 3, and SEQ ID NO: 4 are preferred, and the amino acid sequence of SEQ ID NO: 1 is more preferred.

The urate oxidase derived from different species according to the present disclosure can be obtained through various manners, including but not limited to natural extraction, chemical synthesis, genetic engineering recombinant expression, etc.

In another preferred embodiment, the urate oxidase is prepared and obtained in such a manner that *E. coli* or yeast is used as a host to construct a recombinant expression strain, and *E. coli* is more preferably used as host bacteria for recombinant expression.

The urate oxidase of the present disclosure is subjected to recombinant expression in *E. coli* to obtain a large amount of urate oxidase, and the expressed urate oxidase can be expressed in the cells, on the cell membranes, or secreted out of the cells. If necessary, methods known to those skilled in the art can be used to obtain high-purity urate oxidase. Examples of these methods include, but are not limited to, centrifugation, bacteria destruction, salting out, ultrafiltration, ion exchange chromatography, hydrophobic chromatography, molecular sieve chromatography, and a combination of various other techniques.

The urate oxidase obtained above can be covalently bound to polyethylene glycol through a linking group using methods known in the art.

In another preferred embodiment, polyethylene glycol directionally modifies the lysine residues on a surface of a spatial structure of urate oxidase. Urate oxidase is covalently connected to the modification group (also referred to as active group) of PEG through an amide bond. The modification groups (also referred to as active group) of polyethylene glycol include, but are not limited to, N-hydroxysuccinimide (NHS), N-hydroxysuccinimidyl carbonate (SC), N-hydroxysuccinimidyl acetate (SCM), N-hydroxysuccinimidyl propionate (SPA), N-hydroxysuccinimidyl butyrate (SBA), N-hydroxysuccinimidyl succinate (SS), etc. The blocking group of polyethylene glycol includes, but is not limited to, monomethoxy, ethoxy, glucose, or galactose, preferably monomethoxy.

In another preferred embodiment, the polyethylene glycol may be linear or branched.

In another preferred embodiment, the relative molecular weight of the polyethylene glycol is not more than 6 KD, preferably 1 KD to 5 KD, more preferably 2 KD, 5 KD, and most preferably 5 KD.

In another preferred embodiment, the present disclosure provides a method for preparing the polyethylene glycol-modified urate oxidase. The method has one or more of the following features:

(1) a modification feed molar ratio of urate oxidase to polyethylene glycol (urate oxidase: polyethylene glycol) ranges from 1:45 to 1:150, preferably from 1:45 to 1:110, more preferably from 1:56 to 1:94.

(2) a coupling reaction system is carbonate buffer with a modification pH range of 9 to 11.

(3) a urate oxidase protein concentration in the coupling reaction system is 10 mg/ml.

The above-mentioned method for preparing the polyethylene glycol-modified urate oxidase can obtain high purity polyethylene glycol-modified urate oxidase by using a variety of purification methods.

In another preferred embodiment, the purification of the modified sample includes, but is not limited to, molecular sieve chromatography, ion exchange chromatography, hydrophobic chromatography, tangential flow ultrafiltration, or combinations thereof. More preferred are molecular sieve chromatography and tangential flow ultrafiltration.

In another aspect of the present disclosure, uses of the above-mentioned polyethylene glycol-modified urate oxidase are provided. The conjugate can achieve long-lasting efficacy in vivo and significantly reduce serum uric acid level, applicable for the treatment of hyperuricemia and gout.

The polyethylene glycol-modified urate oxidase is more suitable as a medicament and its composition for treating chronic hyperuricemia or gout. The main symptoms of hyperuricemia and gout include, but are not limited to, uric acid nephropathy and gouty arthritis.

The administration route of the polyethylene glycol-modified urate oxidase includes, but is not limited to, intravenous injection, subcutaneous injection, intramuscular injection, intraperitoneal injection, etc., preferably intravenous injection, intramuscular injection, and more preferably intramuscular injection.

The polyethylene glycol-modified urate oxidase has lower immunogenicity in vivo.

The low immunogenicity of the polyethylene glycol-modified urate oxidase means that, after intramuscular injection of the polyethylene glycol-modified urate oxidase in human body or animal body, the body does not produce antibodies against polyethylene glycol molecules or produces low titer antibodies against polyethylene glycol molecules, and also does not produce antibodies against urate oxidase.

The polyethylene glycol-modified urate oxidase has a longer half-life in vivo and the efficacy in reducing the uric acid level in the blood after intramuscular injection.

According to some embodiments of the present disclosure, the pharmaceutical composition including the polyethylene glycol-modified urate oxidase of the present disclosure may further include a pharmaceutically acceptable carrier, and the dosage form and mode of administration of the pharmaceutical composition are not particularly limited. For injection preparations, pharmaceutically acceptable carriers can include buffers, preservatives, analgesics, solubilizers, isotonic agents, and stabilizers. For locally administered preparations, pharmaceutically acceptable carriers may include bases, excipients, lubricants, and preservatives. The pharmaceutical compositions of the present disclosure can be formulated in various dosage forms in combination with pharmaceutically acceptable carriers as described above.

Excipients and diluents suitable for use in carriers for pharmaceutical formulations according to some specific examples of the present disclosure may include: lactose, glucose, sucrose, sorbitol, mannitol, xylitol, erythritol, maltitol, starch, acacia, alginates, gel, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

In accordance with some other embodiments of the present disclosure, the pharmaceutical composition of the present disclosure may further include fillers, anticoagulants, lubricants, buffers, osmotic pressure regulators, humectants, fragrances, preservatives, and the like.

According to the embodiments of the present disclosure, under the premise of maintaining the enzyme activity to the maximal extent, the polyethylene glycol-modified urate oxidase and the pharmaceutical composition of the present disclosure can greatly enhance the in vivo stability of urate oxidase and reduce the immunogenicity, and after intramuscular injection, the in vivo efficacy thereof can be equivalent to an in vivo efficacy after intravenous injection of an original patented drug. Therefore, the polyethylene glycol-modified urate oxidase of the present disclosure and the pharmaceutical composition containing the polyethylene glycol-modified urate oxidase can be administered when treating or preventing the hyperuric acid-related diseases.

The term "administration" as used herein refers to the introduction of a predetermined amount of a substance into a patient in a suitable manner. The polyethylene glycol-modified urate oxidase of the present disclosure can be administered through any common route, as long as it can reach the desired tissue. Various administration routes are conceivable, including peritoneal, intravenous, intramuscular, subcutaneous, cortical, oral, topical, nasal, pulmonary, and rectal administrations. The present disclosure is not limited to these illustrative administration routes. However, during oral administration, the active ingredients of the orally administered composition should be coated or formulated to prevent their degradation in the stomach. Preferably, the composition of the present disclosure can be administered in the form of injections. In addition, the pharmaceutical composition of the present disclosure can be administered using a specific device configured to deliver the active ingredient to the target cells.

The administration frequency and dose of the pharmaceutical composition of the present disclosure can be determined based on a number of related factors, including the type of disease to be treated, the administration route, the patient's age, gender, and weight, and the severity of the disease, as well as the type of the medicament serving as the active ingredient.

The term "therapeutically effective amount" refers to an amount of a compound that is sufficient to significantly ameliorate certain symptoms associated with a disease or condition, that is, an amount that provides a therapeutic effect for a given condition and dose regimen. For example, in the treatment of chronic hyperuricemia or gout, drugs or compounds that reduce, prevent, delay, inhibit, or block any symptoms of a disease or disorder should be therapeutically effective. A therapeutically effective amount of the drug or compound is not necessarily to cure the disease or condition, but will provide treatment for the disease or condition such that the onset of the disease or condition of an individual is delayed, blocked, or prevented, or the symptoms of the disease or condition are alleviated, or the duration of the disease or condition is changed, or, for example, the disease or illness becomes less serious, or recovery is accelerated.

The term "treatment" is used to refer to obtaining a desired pharmacological and/or physiological effect. Said effect may be prophylactic in terms of complete or partial prevention of the disease or its symptoms, and/or may be therapeutic in terms of partial or complete cure of the disease and/or adverse effects caused by the disease. The "treatment" as used herein covers the treatment of diseases of mammals, especially human (mainly referring to the hyperuric acid-related diseases), including: (a) prevention of diseases in individuals who are prone to a disease but have not yet been diagnosed; (b) inhibition of a disease, such as blocking the development of the disease; or (c) alleviation of a disease, such as reducing the symptoms associated with the disease. The "treatment" as used herein encompasses any medication that administers a medicament or compound to an individual to treat, cure, alleviate, ameliorate, reduce or inhibit the individual's disease, including but not limited to administering the polyethylene glycol-modified urate oxidase described herein to the individual in need thereof.

According to the embodiments of the present disclosure, the polyethylene glycol-modified urate oxidase or pharmaceutical composition of the present disclosure can be used in combination with conventional treatment methods and/or therapies, or can be used separately with conventional treatment methods and/or therapies. When the polyethylene glycol-modified urate oxidase or pharmaceutical composition of the present disclosure is administered in combination therapy with other drugs, they can be administered to the individual sequentially or simultaneously. Alternatively, the pharmaceutical composition of the present disclosure may include a combination of the polyethylene glycol-modified urate oxidase of the present disclosure, a pharmaceutically acceptable carrier or pharmaceutically acceptable excipient, and other therapeutic or preventive drugs known in the art.

The term "average modification degree" refers to the number of PEGs bound to each uricase monomer.

In the present disclosure, unless otherwise specified, the expression "amino acid site has PEG modification" means that, in a three-dimensional structure of a corresponding polypeptide, the PEG molecule covers the amino acid site in such a manner that at least a part of groups at the amino acid site is not exposed. Those skilled in the art can understand that, they can determine whether a specific amino acid site is modified by a PEG molecule through conventional technical means, for example, referring to the method listed in the "Detection of Polyethylene Glycol-Modified Sites" in Example 3 of the present disclosure. In short, the method includes: 1) digesting the non-pegylated and pegylated urate oxidases with one or more enzymes, for example, single-enzyme digestion by using Lys-C or Trypsin, or double-enzyme digestion by using Lys-C and Trypsin; 2) separating the digested fragments by high performance liquid chromatography to generate chromatograms of non-pegylated and pegylated urate oxidases, that is, peptide maps; and 3) comparing the peptide maps of the non-pegylated and pegylated urate oxidases to obtain the difference therebetween, and in combination with a predetermined internal standard peptides, determining a relative proportion of reduction or disappearance of peaks of the peptide fragment where specific amino acid sites are located in the pegylated urate oxidase, and further determining whether the specific amino acid sites on the peptide fragment are modified by PEG. Specifically, in Example 3 of the present disclosure, the relative proportion of the reduction or disappearance of the peak area of the peptide fragment where the specific amino acid sites are located can be calculated according to the following equation:

$$P(\%)=(A_2-A_1)/A_2 100\%, \text{ where } A_1=A_0 \times t.$$

$A_0$ is a measured peak area of a peptide fragment where a specific amino acid site of the modified protein to be tested is located, and t is an average ratio of a peak area of the internal reference peptide fragment in a PHC peptide map to that in the peptide map of the modified protein to be tested; P (%) represents a relative proportion of reduction or disappearance of the peak area of the peptide fragment where the specific amino acid site is located, $A_2$ is a peak area of the peptide fragment where the specific amino acid site is located in the PHC peptide map, and $A_1$ is an internal reference-converted peak area of the peptide fragment where the specific amino acid site is located in the peptide map of the modified protein to be tested.

It should be understood that, within the scope of the present disclosure, the above-mentioned technical features of the present disclosure and the various technical features specifically described as below (such as in the embodiments) can be combined with each other to form a new or preferred technical solution, which can be understood more clearly by referring to the following examples. Due to limited length, the described examples are for illustrative purposes only and are not intended to limit the present disclosure.

Hereinafter, the embodiments of the present disclosure will be described in further detail, and examples of the embodiments are illustrated in the accompanying drawings. The following embodiments described with reference to the accompanying drawings are illustrative, and are intended to explain the present disclosure, but should not be understood as limitations on the present disclosure.

Example 1 Preparation of Recombinant Urate Oxidase

1.1 Construction of Genes and Expression Plasmids for Uricase Expression

According to the usage preference data of *E. coli* codon, in combination with factors such as codon preference and GC content, cDNA sequence of the uricase protein (referred to as PHC) (SEQ ID NO:1) was designed, and the whole gene was synthesized and named as pUC-57-PHC plasmid. Nde I and BamH I were used as the target gene insertion sites, and the pET-30a plasmid was used as the expression vector (pET-30a-PHC).

1.2 Transformation of Expression Plasmids into Bacterial Host Cells

The expression vector pET-30a-PHC was introduced into *E. coli* BL21 (DE3) by CaC12 method, high expression clones were screened through resistance screening with Kanamycin, and the original seed bank strain (E3B) was preserved. These steps were performed in accordance with the commonly used methods in the field of molecular biology.

1.3 Preparation of Recombinant Urate Oxidase

The transformed and engineered strains were fermented and expressed in a fermentor, under the control conditions: first culturing at 30° C. and pH 7.2 to an $OD_{600}$=30 or higher, then increasing the temperature to about 37° C., adding IPTG to 0.5 mmol/L, and continuing to induce for 3 hours or more to allow urate oxidase to accumulate. The cells were collected by centrifugation, and then preserved below −15° C.

The frozen bacteria were taken and suspended in a buffer of 25 mmol/L Tris and 5 mmol/L EDTA, at a suspension ratio of 1:10 (W/V). After breaking the bacterial cells with high pressure, the urate oxidase precipitate was collected by centrifugation, the precipitate was washed once with 50 mmol/L $NaHCO_3$, and the enriched uricase precipitate was suspended in a $Na_2HCO_3$ buffer (100 mmol/L, pH 9.7 to 10.3) at a suspension ratio of 1:50 (W/V), following by stirring overnight at room temperature to dissolve, and then centrifuging to collect the supernatant.

Urate oxidase was further purified through several chromatographic steps. The purity detected by SDS-PAGE was 95% or greater, and the purity detected by Superdex 200 column was greater than 95%, with no aggregate form. The protein concentration was determined by Lowry method, and the activity of the urate oxidase was measured by spectrophotometry, where 1 unit (U) of enzyme activity was defined as the amount of enzyme required to convert 1 μmol of uric acid per minute under the reaction temperature of 37° C. and the optimal buffer condition at pH 9.0.

Example 2 Preparation of Pegylated Urate Oxidase

Monomethoxy PEG derivatives with different molecular weights (500 Da to 20,000 Da), such as N-succinimidyl propionate PEG (5K-PEG-SPA) with a molecular weight of 5 K, are dissolved with a 1 to 5 mmol/L acid solution to form a 100 to 300 mmol/L PEG solution, which, after the dissolving, was added to a carbonate buffer solution containing the urate oxidase dissolved therein and having a carbonate concentration of 0.1 to 0.3 mol/L, pH 10.0, according to molar ratio of 1:45 to 1:150 (urate oxidase: 5K-PEG-SPA), thereby allowing a coupling reaction between PEG and urate oxidase. A concentration of the urate oxidase in the coupling reaction was 10 mg/ml. The coupling reaction required stirring at 5 to 30° C. for 60 minutes or more, until the PEG coupling degree no longer changed with time. After the reaction was finished, the PEG not participating in the modification and by-products were removed from the reaction by ultrafiltration and/or chromatography. A suitable molecular sieve chromatography medium was used to separate and remove modified by-products. Finally, the 5 K modified pegylated urate oxidase (referred to as PU5) was obtained through sterile filtration.

Example 3: Characteristic Analysis of Pegylated Urate Oxidase 3.1 Detection of Average Modification Degree and Enzyme Activity The protein concentration was determined by using Lowry method, and the activity of the polyethylene glycol-modified urate oxidase was determined by using spectrophotometer. The maximum ultraviolet absorption wavelength of uric acid, i.e., the substrate of uricase, was 293 nm, and the maximum ultraviolet absorption wavelength of the product allantoin was 224 nm. Within a certain concentration range, the absorption value of uric acid at 293 nm was in direct proportion to its concentration. The quantitative determination of uric acid can be carried out by spectrophotometer. The specific process was as follows: the UV-Vis spectrophotometer was turned on, the wavelength was adjusted to 293 nm, and the water bath circulation system of the instrument was turned on to keep the temperature at 37° C. Sodium tetraborate buffer was used as a blank control, and zero point was calibrated; 2.95 ml of substrate reaction solution (0.1 mol/L sodium tetraborate, 100 μmol/L uric acid, pH 9.5, preheated to 37° C.) was added in a quartz cuvette, then 50 μl of the test sample was added and mixed quickly to measure the absorption value at 293 nm. The change of the absorbance at 293 nm was continuously measured; a degradation concentration of uric acid was calculated according to $C=A/\varepsilon L$ (where A is an absorbance of a specific concentration of uric acid at 293 nm, c is a molar extinction coefficient of uric acid, L is an optical path of the cuvette, and C is a molar concentration of uric acid). The enzyme activity was calculated. The enzyme activity was defined as that, at the optimum reaction temperature of 37° C. and the optimum reaction pH 9.5, the amount of enzyme required to convert 1 μmol of uric acid into allantoin per minute is defined as one activity unit (U).

SEC-HPLC connected in series with UV/RI (a combination of ultraviolet and refractive index detector) was used to detect the average modification degree of polyethylene glycol-modified urate oxidase. Based on the fact that protein has a maximum absorption peak at ultraviolet 280 nm, PEG has no absorption at this wavelength, and the absorption value of the protein and the absorption value of PEG within a certain range by the differential refractive index detector are proportional to the respective concentrations, the content of PEG portion and the content of protein portion in the pegylated urate oxidase can be obtained using an external standard method with PEG reference substance and PHC physical and chemical reference substance, and thus the number of PEG molecules on each urate oxidase monomer, i.e., the average modification degree, can be obtained by the following calculation method.

Average modification degree of PEG-modified urate oxidase=(relative molecular weight of urate oxidase subunit×amount of PEG in sample)/(relative molecular weight of PEG×amount of protein in sample).

The SEC-HPLC-UV/RI detection spectrums of PHC physical and chemical reference substance, PEG reference substance, and PU5 modified product are illustrated in FIG. 1 to FIG. 5.

Under different feed ratios in Example 2, the enzyme activity and average modification degree of the obtained polyethylene glycol-modified urate oxidase are shown in Table 1.

TABLE 1

Enzyme activity and average modification degree at different feed ratios at 5K-PEG

| Protein:5K-PEG feed molar ratio | Enzyme activity | Enzyme activity retention | Average modification degree |
|---|---|---|---|
| Unmodified urate oxidase | 11.4 U/mg | 100% | 0 |
| 1:48 | 10.71 U/mg | 94% | 10.3 |
| 1:56 | 11.17 U/mg | 103.4% | 11.4 |
| 1:68 | 12.2 U/mg | 107.1% | 11.9 |
| 1:82 | 12.02 U/mg | 105.4% | 12.3 |
| 1:94 | 11.75 U/mg | 103.1% | 12.1 |
| 1:110 | 10.83 U/mg | 95% | 11.5 |
| 1:150 | 10.03 U/mg | 88% | 10.1 |

The enzyme activity and the average modification degree of polyethylene glycol-modified urate oxidase obtained at different molecular weights of PEG and a feed molar ratio of protein to PEG of 1:68 in Example 2 are shown in Table 2.

TABLE 2

Enzyme activity and average modification degree under modification at different molecular weights of PEG

| PEG MW(KD) | Average modification degree | Enzyme activity (U/mg) | Enzyme activity retention |
|---|---|---|---|
| 0 | — | 11.3 | 100% |
| 2 | 11.7 | 11.6 | 102.7% |
| 3.5 | 11.5 | 11.4 | 100.9% |
| 5 | 11.8 | 12.1 | 107.1% |
| 10 | 11.7 | 11.8 | 104.4% |

Notes:
the average modification degree represents the number of PEG molecules on each urate oxidase monomer.

It can be seen from Table 1 and Table 2 that the polyethylene glycol-modified urate oxidase of the present disclosure has an average modification degree of 11 or more, and the enzyme activity was higher than that of unmodified urate oxidase, the enzyme activity retention was high, the enzyme activity is even increased instead of decreasing, and the enzyme activity was relatively stable. This is inconsistent with the viewpoint taught by the original patented drug that the low-molecular-weight PEG modification will lead to a decrease in enzyme activity, and the polyethylene glycol-modified urate oxidase obtained in the present disclosure has a higher average modification degree with polyethylene glycol, thus achieving unexpected technical effects in terms of enzyme activity retention.

Meanwhile, the inventors measured the immunogenicity of urate oxidase obtained under the modification of PEGs with different molecular weights, and the experimental results are shown in Table 3.

TABLE 3

In vivo antibody results of urate oxidase modified by PEGs with different molecular weights in mice

| PEG MW(KD) | Average modification degree | Anti-PEG antibody: Antibody positive rate | Anti-PEG antibody: Antibody titer range | Anti-uricase protein antibody: Antibody positive rate | Anti-uricase protein antibody: Antibody titer range |
|---|---|---|---|---|---|
| 0 (unmodified) | — | 0/8 | — | 8/8 | 1:51200 to 1:204800 |
| 2 | 11.7 | 1/8 | 1:100 to 1:400 | 2/8 | 1:100 to 1:300 |
| 3.5 | 11.5 | 1/8 | 1:100 to 1:600 | 2/8 | 1:50 to 1:100 |
| 5 | 11.8 | 2/8 | 1:100 to 1:700 | 1/8 | 1:20 to 1:50 |
| 10 | 11.7 | 4/8 | 1:1600 to 1:12800 | 2/8 | 1:50 to 1:100 |

In the experiment, mice were divided into groups with 8 mice in each group. Intravenous administration of 1 mg/kg was given to each animal once a week. After four consecutive times of administration, blood samples were collected to evaluate the anti-PEG and anti-urate oxidase immunogenicity. As can be seen from the results in Table 3, in the case of consistent average modification degree, as the molecular weight of PEG increases, the positive rate of anti-PEG antibody generated increases, and when the molecular weight of PEG exceeds 5 KD, the positive rate of anti-PEG antibody and antibody titer significantly increase. It can be seen from the analysis of anti-urate oxidase results that PEG modification can significantly reduce the antibody positive rate and antibody titer of urate oxidase, and in the case of consistent average modification degree, in the range of 2 K to 5 K, the generated anti-urate oxidase antibody positive rate and antibody titer become lower with the increase of PEG molecular weight, while when the PEG molecular weight is greater than 5K, the risk of anti-uricase antibody will also occur. In conclusion, 2 to 5 K PEG modified urate oxidase is superior to 10K PEG modified urate oxidase, and 5 KD is more preferred.

Finally, the inventors measured the enzyme activity and the average modification degree of urate oxidase obtained by modification with PEGs dissolved with different acids. The acid solution used may be selected from organic acids such as acetic acid, oxalic acid, maleic acid, tartaric acid, citric acid, succinic acid, malonic acid, adipic acid, ascorbic acid, benzenesulfonic acid, benzoic acid, butyric acid, cyclopentylpropionic acid, digluconic acid, dodecylsulfuric acid, ethanesulfonic acid, formic acid, fumaric acid, glucoheptonic acid, glycerophosphoric acid, gluconic acid, heptanoic acid, hexanoic acid, 2-hydroxyethanesulfonic acid, digalacturonic acid, lactic acid, lauric acid, laurylsulfuric acid, malic acid, malonic acid, methanesulfonic acid, 2-naphthalenesulfonic acid, nicotinic acid, oleic acid, palmitic acid, pectic acid, 3-phenylpropionate, picrate, pivalic acid, propionic acid, stearic acid, p-toluenesulfonic acid, undecanoic acid, and valeric acid; and may also be selected from inorganic acids such as hydrochloric acid, hydrobromic acid, phosphoric acid, sulfuric acid, perchloric acid, hydriodic acid, nitric acid, peroxydisulfuric acid, boric acid, dichromic acid, silicic acid, chromic acid, and thiocyanic acid. Different types of acid solutions can achieve the dissolution of PEG and uricase modification. The different PEG feed ways and feed ratios are shown in Table 4 below.

TABLE 4

Influence of different feed ways and feed ratios on PEG modification results

| PEG feed ways | Feed ratios (molar feed ratio) Protein:5K-PEG | Average modification degree | Enzyme activity |
|---|---|---|---|
| Feeding with Dry powder | 1:48 | 8.8 | 8.96 U/mg |
| | 1:56 | 9.3 | 9.18 U/mg |
| | 1:94 | 9.8 | 9.26 U/mg |
| | 1:110 | 9.2 | 9.16 U/mg |
| Dissolving with hydrochloric acid | 1:48 | 10.8 | 10.96 U/mg |
| | 1:56 | 11.4 | 11.21 U/mg |
| | 1:94 | 12.4 | 11.35 U/mg |
| | 1:110 | 12.2 | 10.76 U/mg |
| Dissolving with sulfuric acid | 1:94 | 11.9 | 11.16 U/mg |
| Dissolving with glacial acetic acid | 1:94 | 11.7 | 11.03 U/mg |

The inventors found that dissolving PEG with acid before feeding results in a higher protein modification rate and higher enzyme activity, and significant saves the amount of PEG used compared with feeding directly with dry powder.

3.2 Detection of Polyethylene Glycol Modification Sites

In the following steps, the inventors performed modification site detection on an existing drug on the market and the urate oxidase obtained in the Example.

The PEG modification sites of polyethylene glycol-modified urate oxidase can be detected by first performing enzyme digestion of the non-pegylated and pegylated urate oxidases with one or more enzymes and then performing chromatographic detection to obtain a chromatogram, i.e., peptide map for determination. The non-pegylated and pegylated urate oxidases can be digested through single-enzyme digestion (Lys-C or Trypsin) and/or double-enzyme digestion (Lys-C and Trypsin combined). The digested enzyme fragments were separated by reversed-phase column, and the modification sites of polyethylene glycol-modified urate oxidase and the PEG modification percentage of the sites were calculated by the internal reference peptide fragment correction and comparison of the disappearance or reduction proportion of the peptide fragments.

Modification site analysis principle of trypsin and Lys-C double enzyme digestion quality peptide map: Lys-C can specifically digest the C-terminal of lysine (K); trypsin takes the basic amino acids, i.e., arginine (R) and lysine (K), as restriction enzyme cutting sites, and specifically digests the C-terminal peptide bond. Comparing the changes of the corresponding peptide fragments before and after digestion in PHC and PU5, and with reference to the internal standard peptide fragments, the relative proportion of the reduction or disappearance of the PEG-modified peptide fragments can be analyzed and determined. Through the relative proportion of the reduction or disappearance of the peptide fragment, a relative percentage of PEG modification at the lysine site on the peptide fragment can be determined, thereby determining whether a specific amino acid (e.g., lysine) on a specific peptide fragment is modified by PEG.

Details as follows:

(1) Sample processing: urate oxidase and pegylated urate oxidase were taken and respectively diluted to 1 mg/mL with enzyme digestion buffer (25 mmol/L Tris-HCl, 20% acetonitrile, pH 9.0), and 100 μl of each dilute solution was taken, added with 2 μL of Lys-C, and digested at 37° C. for 4 hours. Subsequently, the solution was transferred to a pancreatin reaction tube (in a ratio of 1:100), digestion was continued at 37° C. for 2 hours, 4 μL of TCEP reducing solution was added, the reaction continued for 30 minutes, and then 10 μL of 1 mol/L hydrochloric acid solution was added to terminate the reaction.

(2) Analysis conditions:

Instrument: Thermo Ultimate 3000 HPLC and MSQ Plus;

Chromatographic column: Welch Materials μltimate®gXB-C18 (4.6 mm×250 mm, 5 μm), Welch;

Analysis conditions: A solution (aqueous solution containing 0.1% TFA), solution B (acetonitrile solution containing 0.1% TFA);

Gradient: 0 to 70 min, B from 3 to 70%;

LC detection wavelength: 214 nm;

Ion source: ESI;

Ion type: positive ion;

Cone voltage: 50V;

Scanning range: 300 to 2000 Da;

Scan time: 1 s;

Post column flow splittered to MS: about 0.3 mL/min.

100 μL of the sample was injected, and the chromatogram was recorded.

(3) Results processing:

The chromatograms (peptide maps) of urate oxidase and pegylated urate oxidase were compared, and the relative proportion of area reduction of the differential peptide fragments.

Figure 6:
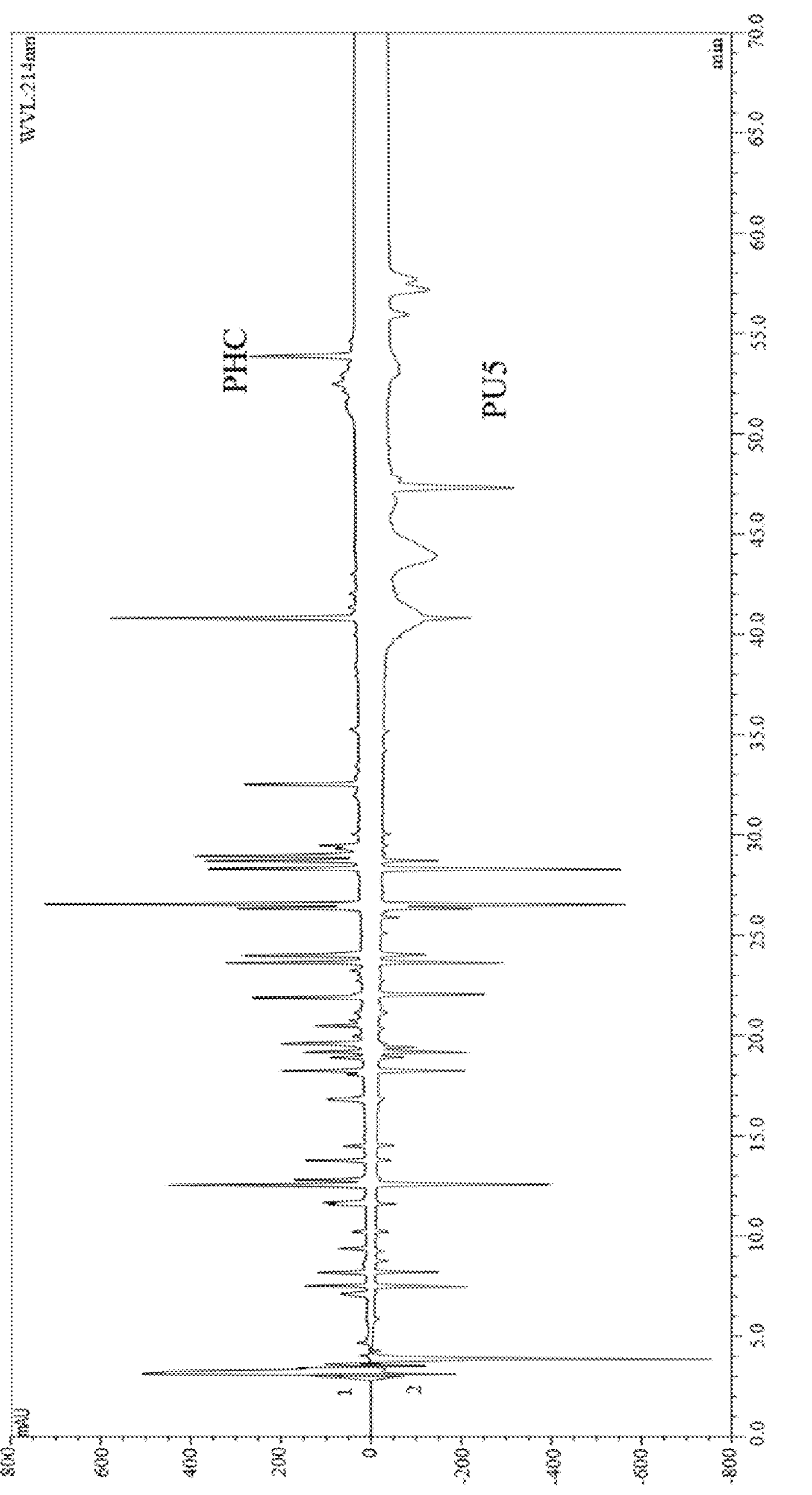
FIG. 6 is a comparison diagram of PHC and PU5 using Lys-c and trypsin double digestion according to an embodiment of the present disclosure.
Figure 7:
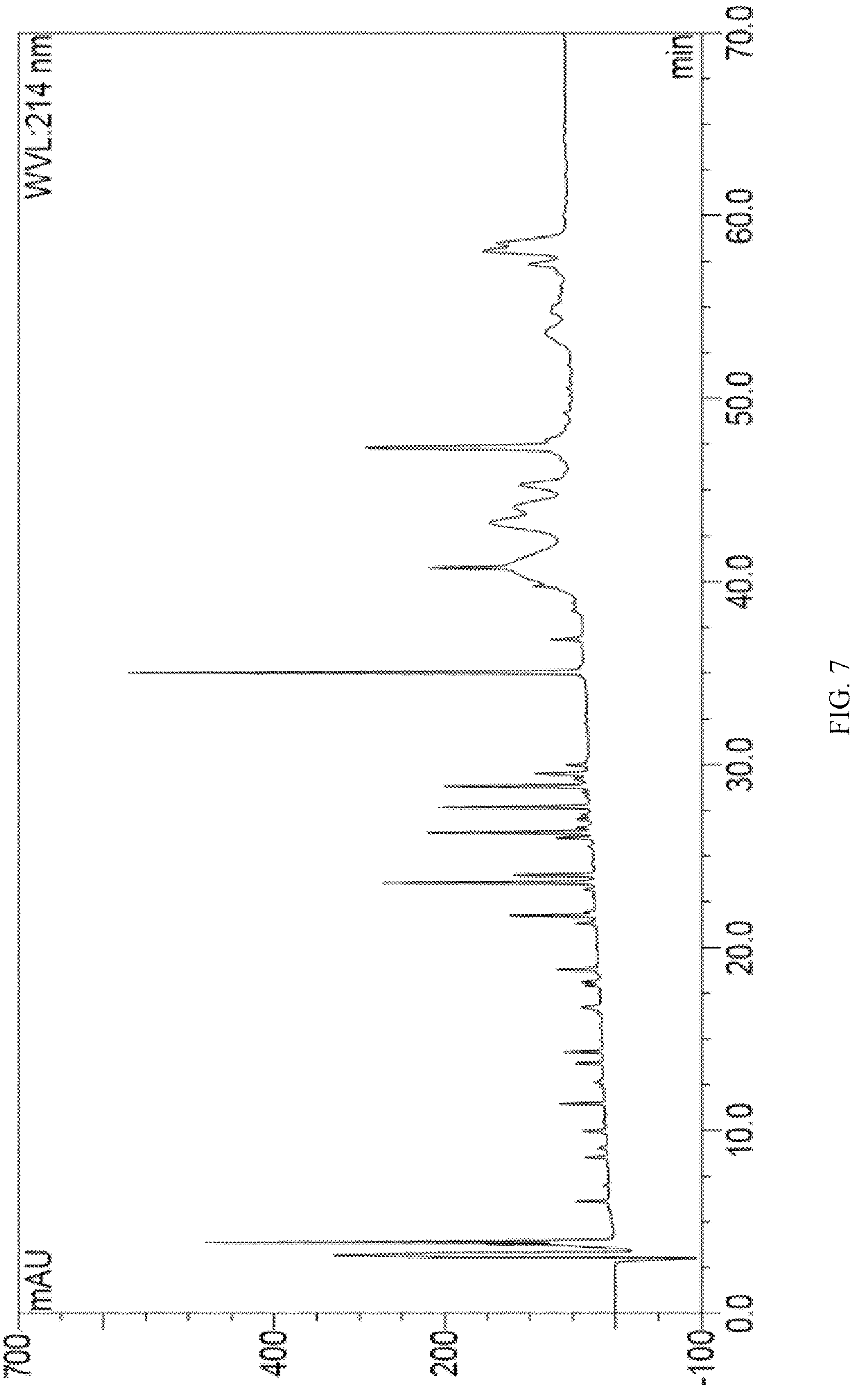
FIG. 7 is a diagram of Lys digestion of PU5 according to an embodiment of the present disclosure.

(4) The experimental results are shown in Table 5 to Table 8, and FIG. 6 to FIG. 7.

TABLE 5

List of peptide fragments of PHC after digestion with Lys-C

| Peptide fragment | Digestion site | Sequence | Theoretical molecular weight (Da) | Measured molecular weight |
|---|---|---|---|---|
| T1 | 3 | TYK | 410.47 | 410.2 |
| T2 | 4 | K | 146.189 | —/ |
| T3 | 17 | NDEVEFVRTGYGK | 1513.627 | —/ |
| T2 + T3 | | KNDEVEFVRTGYGK | 1641.089 | 1642.2 |
| T4 | 21 | DMIK | 505.63 | 505.4 |
| T5 | 30 | VLHIQRDGK | 1065.241 | 1065 |
| T6 | 35 | YHSIK | 646.744 | 646.5 |
| T7 | 48 | EVATTVQLTLSSK | 1376.57 | —/ |
| T8 | 49 | K | 146.189 | —/ |
| T9 | 66 | DYLHGDNSDVIPTDTIK | 1903.032 | 1903 |
| T10 | 74 | NTVNVLAK | 858.005 | 857.7 |
| T11 | 76 | FK | 293.366 | 293.1 |
| T12 | 79 | GIK | 316.401 | 316.2 |
| T13 | 97 | SIETFAVTICEHFLSSFK | 2059.364 | 2059 |
| T14 | 112 | HVIRAQVYVEEVPWK | 1853.154 | 1852.8 |
| T15 | 116 | RFEK | 578.669 | 578.4 |

TABLE 5-continued

| List of peptide fragments of PHC after digestion with Lys-C | | | | |
|---|---|---|---|---|
| Peptide fragment | Digestion site | Sequence | Theoretical molecular weight (Da) | Measured molecular weight |
| T16 | 120 | NGVK | 416.478 | 417.2 |
| T17 | 152 | HVHAFIYTPTGTHFCEVE QIRNGPPVIHSGIK | 3586.088 | 3586.2 |
| T18 | 155 | DLK | 374.437 | 374.1 |
| T19 | 158 | VLK | 358.481 | 358.2 |
| T20 | 169 | TTQSGFEGFIK | 1214.34 | 1213.8 |
| T21 | 179 | DQFTTLPEVK | 1177.32 | 1176.8 |
| T22 | 190 | DRCFATQVYCK | 1333.543 | 1333.2 |
| T23 | 215 | WRYHQGRDVDFEATWD TVRSIVLQK | 3106.45 | 3106.5 |
| T24 | 222 | FAGPYDK | 796.878 | 796.5 |
| T25 | 231 | GEYSPSVQK | 994.069 | 993.7 |
| T26 | 266 | TLYDIQVLTLGQVPEIED MEISLPNIHYLNIDMSK | 4046.66 | 4046.1 |
| T27 | 272 | MGLINK | 674.856 | |
| T28 | 285 | EEVLLPLDNPYGK | 1486.685 | 1486.6 |
| T27 + T28 | | MGLINK EEVLLPLDNPYGK | 2143.54 | 2143.2 |
| T29 | 291 | ITGTVK | 617.743 | 617.4 |
| T30 | 293 | RK | 302.377 | |
| T31 | 298 | LSSRL | 574.678 | 574.4 |

TABLE 6

| List of peptide fragments of PHC after double-enzyme digestion with Lys-C and trypsin | | | | |
|---|---|---|---|---|
| Peptide fragment | Sequence position | Sequence | Theoretical relative molecular weight [Da] | Measured molecular weight |
| T1 | 1-3 | TYK | 410.470 | 410.3 |
| T2 | 4 | K | 146.189 | / |
| T3 | 5-12 | NDEVEFVR | 1007.068 | / |
| T2 + 3 | 4-12 | KNDEVEFVR | | 1135.4 |
| T4 | 13-17 | TGYGK | 524.574 | 524.5 |
| T5 | 18-21 | DMIK | 505.630 | 505.5 |
| T6 | 22-27 | VLHIQR | 764.926 | 764.8 |
| T7 | 28-30 | DGK | 318.330 | / |
| T8 | 31-35 | YHSIK | 646.744 | 646.7 |
| T9 | 36-48 | EVATTVQLTLSSK | 1376.570 | / |
| T10 | 49 | K | 146.189 | / |

TABLE 6-continued

List of peptide fragments of PHC after double-enzyme digestion with Lys-C and trypsin

| Peptide fragment | Sequence position | Sequence | Theoretical relative molecular weight [Da] | Measured molecular weight |
|---|---|---|---|---|
| T11 | 50-66 | DYLHGDNSDVIPTDTIK | 1903.032 | 1903.4 |
| T12 | 67-74 | NTVNVLAK | 858.005 | 857.9 |
| T13 | 75-76 | FK | 293.366 | 293.1 |
| T14 | 77-79 | GIK | 316.401 | / |
| T15 | 80-97 | SIETFAVTICEHFLSSFK | 2059.364 | 2059.6 |
| T16 | 98-101 | HVIR | 523.636 | 523.6 |
| T17 | 102-112 | AQVYVEEVPWK | 1347.534 | 1347.4 |
| T18 | 113 | R | 174.203 | / |
| T19 | 114-116 | FEK | 422.481 | / |
| T18 + 19 | 113-116 | RFEK | 578.684 | 578.6 |
| T20 | 117-120 | NGVK | 416.478 | 417.1 |
| T21 | 121-141 | HVHAFIYTPTGTHFCEVEQ | 2485.802 | 2486.8 |
| T22 | 142-152 | NGPPVIHSGIK | 1118.301 | 1118.8 |
| T21 + 22 | 121-152 | | 3586.103 | 3587.7 |
| T23 | 153-155 | DLK | 374.437 | / |
| T24 | 156-158 | VLK | 358.481 | 358.3 |
| T25 | 159-169 | TTQSGFEGFIK | 1214.340 | 1214.2 |
| T26 | 170-179 | DQFTTLPEVK | 1177.320 | 1177.2 |
| T27 | 181-181 | DR | 289.291 | / |
| T28 | 182-190 | CFATQVYCK | 1062.267 | / |
| T27 + 28 | 181-190 | | 1333.558 | 1333.6 |
| T29 | 191-192 | WR | 360.416 | 360.1 |
| T30 | 193-197 | YHQGR | 659.702 | 659.6 |
| T31 | 198-209 | DVDFEATWDTVR | 1453.528 | 1453.6 |
| T32 | 210-215 | SIVLQK | 686.850 | 686.8 |
| T33 | 216-222 | FAGPYDK | 796.878 | 796.8 |
| T34 | 223-231 | GEYSPSVQK | 994.069 | 994.1 |
| T35 | 262-266 | TLYDIQVLTLGQVPEIEDM EISLPNIHYLNIDMSK | 4046.660 | 4047 |
| T36 | 267-272 | MGLINK | 674.856 | 674.7 |
| T37 | 273-285 | EEVLLPLDNPYGK | 1486.685 | 1486.7 |
| T36 + 37 | | | 2143.541 | 2143.6 |
| T38 | 286-291 | ITGTVK | 617.743 | 617.7 |
| T39 | 292 | R | 174.203 | / |
| T40 | 293 | K | 146.189 | / |

TABLE 6-continued

List of peptide fragments of PHC after double-enzyme digestion with Lys-C and trypsin

| Peptide fragment | Sequence position | Sequence | Theoretical relative molecular weight [Da] | Measured molecular weight |
|---|---|---|---|---|
| T41 | 294-297 | LSSR | 461.519 | 461.5 |
| T42 | 298 | L | 131.175 | / |

The calculation method of the reduction percentage of peak area of PU5 peptide fragments is as follows:

The following formula can be used to calculate the corresponding peak areas of PU5 peptide fragments at the concentration of PU5 same as the concentration of PHC:

$$A_1 = A_0 \times t$$

where $A_1$ is a peak area of PU5 peptide fragments converted with two internal reference peptides, $A_0$ is a measured peak area of peptide fragments of a PU5 peptide map, and t is an average value of a peak area ratio of T30 internal reference peptide fragment in the PHC peptide map to T30 internal reference peptide fragment in the PU5 peptide map and a peak area ratio of T31 internal reference peptide fragment in the PHC peptide map to T31 internal reference peptide fragment in the PU5 peptide map, that is, t is 0.588.

TABLE 7

Comparison of PHC and PU5 internal reference peptide fragments

| Peptide No. fragment | Sequence | PHC peptide map Retention time | PHC peptide map Peak area | PU5 peptide map Retention time | PU5 peptide map Peak area | Peak area ratio of PHC to PU5 Value | Peak area ratio of PHC to PU5 Mean |
|---|---|---|---|---|---|---|---|
| T30 | YHQGR | 7.5 | 13.4 | 7.467 | 22.9 | 0.585 | 0.588 |
| T31 | DVDFEATWDTVR | 28.31 | 35.5 | 28.28 | 60.1 | 0.591 | |

With the peak area of peptide fragment converted with the internal reference and the peak area of PHC peptide map, the relative percentage of the reduction of the peak area of a certain peptide in the PU5 peptide map can be calculated based on the following equation:

$$P(\%) = (A_2 - A_1)/A_2 \times 100\%$$

where $A_2$ is a peak area of a certain peptide fragment in the PHC peptide map, and $A_1$ is a peak area of this peptide fragment in PU5 converted with internal reference.

TABLE 8

Summary results of peptide fragments with reduced peak area in the peptide map after PU5 was digested with double enzymes.

| Peptide fragment position | Peptide fragment sequence | Relative proportion of reduced peak area of peptide fragment |
|---|---|---|
| 1-3 | TYK | 100.00% |
| 4-12 | KNDEVEFVR | 94.07% |
| 31-35 | YHSIK | 100.00% |
| 75-76 | FK | 82.27% |
| 80-97 | SIETFAVTICEHFLSSFK | 100.00% |
| 102-112 | AQVYVEEVPWK | 100.00% |
| 113-116 | RFEK | 100.00% |
| 117-120 | NGVK | 100.00% |

TABLE 8-continued

Summary results of peptide fragments with reduced peak area in the peptide map after PU5 was digested with double enzymes.

| Peptide fragment position | Peptide fragment sequence | Relative proportion of reduced peak area of peptide fragment |
|---|---|---|
| 121-152 | HVHAFIYTPTGTHFCEVEQIRNGPPVIHSGIK | 100.00% |
| 193-197 | YHQGR | Internal reference peptide fragment |
| 198-209 | DVDFEATWDTVR | Internal reference peptide fragment |
| 216-222 | FAGPYDK | 91.37% |
| 223-231 | GEYSPSVQK | 86.40% |
| 232-266 | TLYDIQVLTLGQVPEIEDMEISLPNIHYLNIDMSK | 100.00% |
| 273-285 | EEVLLPLDNPYGK | 100.00% |

Based on the analysis of the protein sequence (SEQ ID NO: 1) of the present example, the potential sites for urate oxidase modification include 31 sites, including $T^1$, $K^3$, $K^4$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, and $K^{293}$.

Based on the analysis of the modification sites of polyethylene glycol-modified urate oxidase obtained in Example 2, as shown in Table 5, Table 6, Table 7, Table 8 and FIG. 6, the sites with 90% or more disappearance of the peptide fragments after PU5 digestion include $K^3$, $K^4$, $K^{35}$, $K^{97}$, $K^{112}$, $K^{116}$, $K^{120}$, $K^{152}$, $K^{222}$, $K^{266}$, and $K^{285}$, the sites with 80% to 90% disappearance of the peptide fragments after PU5 digestion include $K^{76}$ and $K^{231}$.

Moreover, the inventors found that the polyethylene glycol-modified urate oxidase of the present disclosure has more modification sites than the marketed drug, and has significant differences. For example, through single enzyme digestion, it was found that the disappearance ratio of the peptide fragments where the four sites $K^{30}$, $K^{35}$, $K^{222}$, and $K^{231}$ are located in the polyethylene glycol-modified urate oxidase of the present disclosure is more than 80%, while the peptide fragments of the marketed analogous drug where these four sites are located hardly disappeared, that is, the modification rate of the marketed analogous drug at the four sites $K^{30}$, $K^{35}$, $K^{222}$, and $K^{231}$ is much lower than that of the polyethylene glycol-modified urate oxidase of the present disclosure. In addition, the polyethylene glycol-modified urate oxidase of the present disclosure has significantly lower immunogenicity than the marketed drug, which may be related to the differences in the number of modification sites and the modification sites according to Applicant's speculation.

The in vivo evaluation of the polyethylene glycol-modified urate oxidase (PU5) of the present disclosure in animals will be described in detail as below. The pegloticase used in the experiment refers to the analogous drug on the market with a batch number 5085B.

Example 4 Study on In Vivo Pharmacodynamics of Polyethylene Glycol-Modified Urate Oxidase

4.1. In Vivo Efficacy Evaluation of Polyethylene Glycol-Modified Urate Oxidase in Model Rats A chronic hyperuricemia rat model was induced by potassium oxazinate drinking water in combination with high uric acid feed, to evaluate the therapeutic effect of polyethylene glycol-modified urate oxidase (PU5) on chronic hyperuricemia in rats.

40 model rats were selected and randomly divided into 4 groups, i.e., a model group, a low-dose pegylated uricase administration group (0.3 mg/kg), a medium-dose pegylated uricase administration group (1.0 mg/kg), and a high-dose pegylated uricase administration group (3.0 mg/kg), 10 rats in each group; and additionally, 10 normal SD rats were selected as the blank control group. The model-establishing experiment was conducted for 5 consecutive weeks, and intramuscular administration was started 1 week after the start of the model establishing. The administration was performed and continued once a week for 4 consecutive weeks. The levels of serum uric acid, serum urea nitrogen, and serum creatinine of rats before the administration and 7 days after each administration were detected, and the histological changes of rat kidneys were observed after the experiment.

Figure 8:
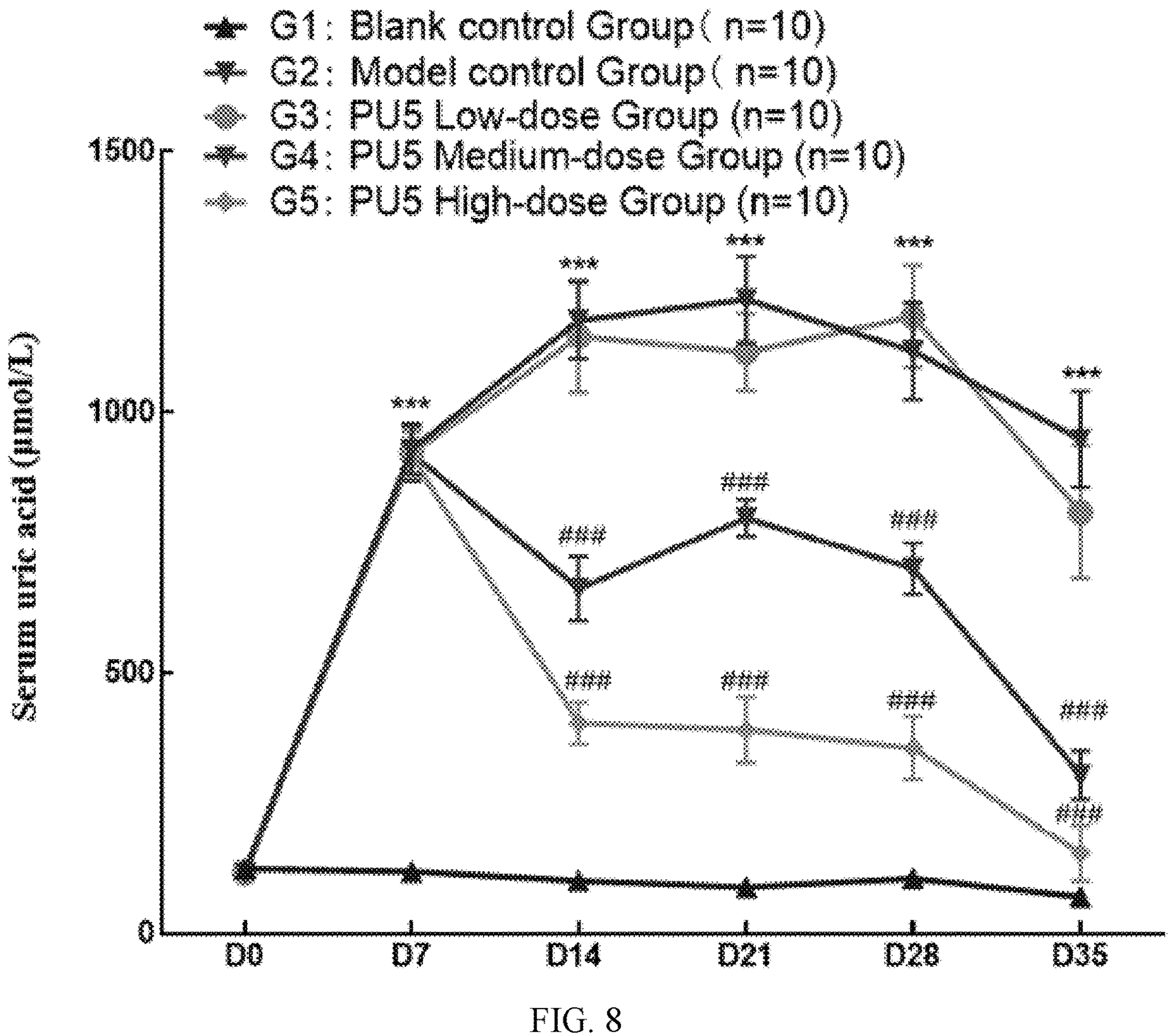
FIG. 8 illustrates serum uric acid levels after intramuscular administration of different doses to model rats according to an embodiment of the present disclosure.
Figure 9:
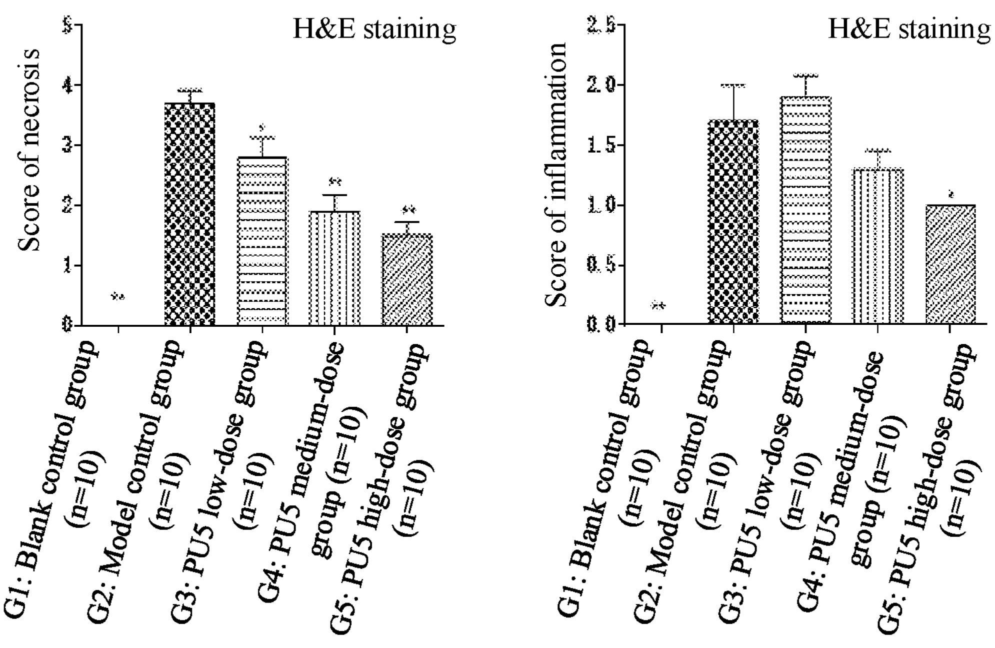
FIG. 9 is a diagram illustrating scores of kidney injury, necrosis, and inflammation according to an embodiment of the present disclosure.

The results in FIG. 8 indicate that on days 7, 14, 21, 28, and 35 after the start of the model establishing, compared with the blank control group, the serum uric acid level of the model control group increased significantly, and the serum urea nitrogen, creatinine and uric acid of the rats in the model group were 2.73 times, 2.40 times and 7.83 times these in the blank group, respectively. From the perspective of kidney pathology (as shown in FIG. 9), the scores of renal tubule dilatation, necrosis, inflammation, and fibrosis of the model control group increased significantly, and the quantity of urate crystals also increased significantly. Both the medium and high doses of the test substance, pegylated uricase, significantly reduced the serum uric acid level, which exhibited a dose-dependent relationship. During the period from day 14 to day 35, the average serum uric acid level of the medium-dose group was maintained at 303.80 to 660.60 μmol/L, and the average serum uric acid level of the high-dose group was maintained at 153.70 to 403.40 μmol/L. Compared with the model group, the serum uric acid in the medium-dose group was reduced by 34.46% to 67.94%; the serum uric acid in the high-dose group was reduced by 65.67% to 83.78%. Compared with the model control group, each pegylated uricase administration group had significant ameliorating effects on the renal tubule dilatation, renal necrosis and inflammation.

4.2 Evaluation of Single Administration of Polyethylene Glycol-Modified Urate Oxidase in Rats 36 SD rats (half females and half males) were randomly divided into 6 groups (see Table 9), namely, a marketed drug Pegloticase intravenous injection group, a Pegloticase intramuscular injection group, a polyethylene glycol-modified urate oxidase intravenous injection group, as well as low-dose, medium-dose and high-dose polyethylene glycol-modified urate oxidase intramuscular injection groups (0.5 mg/kg, 1.0 mg/kg, 2.0 mg/kg). The specific administration regimens and doses are shown in Table 9. PK and PD were detected by taking the blood from the jugular vein.

After administration, for each group of 1.0 mg/kg Pegloticase intravenous injection and intramuscular injection groups, 1.0 mg/kg pegylated uricase intravenous injection group, as well as 0.5 mg/kg, 1.0 mg/kg, and 2.0 mg/kg pegylated uricase intramuscular injection groups, a ratio of Cmax (C5min) of female SD rats to male SD rats was in the range of 0.75 to 0.99, a ratio of AUClast of female SD rats to male SD rats was in the range of 0.54 to 0.94, and a ratio of AUC0-∞ of female SD rats to male SD rats was in the range of 0.58 to 0.97. It can be seen that there is no significant gender difference in the exposure levels of Pegloticase and the pegylated uricase (PU5) injections in SD rats.

However, when the SD rats were administered with the same dose (1.0 mg/kg), AUClast of the marketed drug Pegloticase intravenous administration group was 426.48±65.34, AUClast of the Pegloticase intramuscular injection group was 264.19±78.22; and AUClast of the PU5 injection intravenous administration group was 565.61±161.60, the AUClast of the PU5 intramuscular injection group was 337.86±227.34. Under the same dose and administration mode, the AUClast of PU5 was higher than that of the marketed drug Pegloticase.

When the SD rats were administered with the same dose (1.0 mg/kg), t½ (h) of the marketed drug Pegloticase intravenous administration group was 49.51±8.12, t½ (h) of the Pegloticase intramuscular administration group was 55.21±13.50, t½ (h) of the PU5 injection intravenous administration group was 86.12±33.82, and the t½ (h) of the PU5 intramuscular administration group was 60.45±21.37. Under the same dose and administration mode, the t½ (h) of PU5 was longer than that of the marketed drug Pegloticase.

Figure 10:
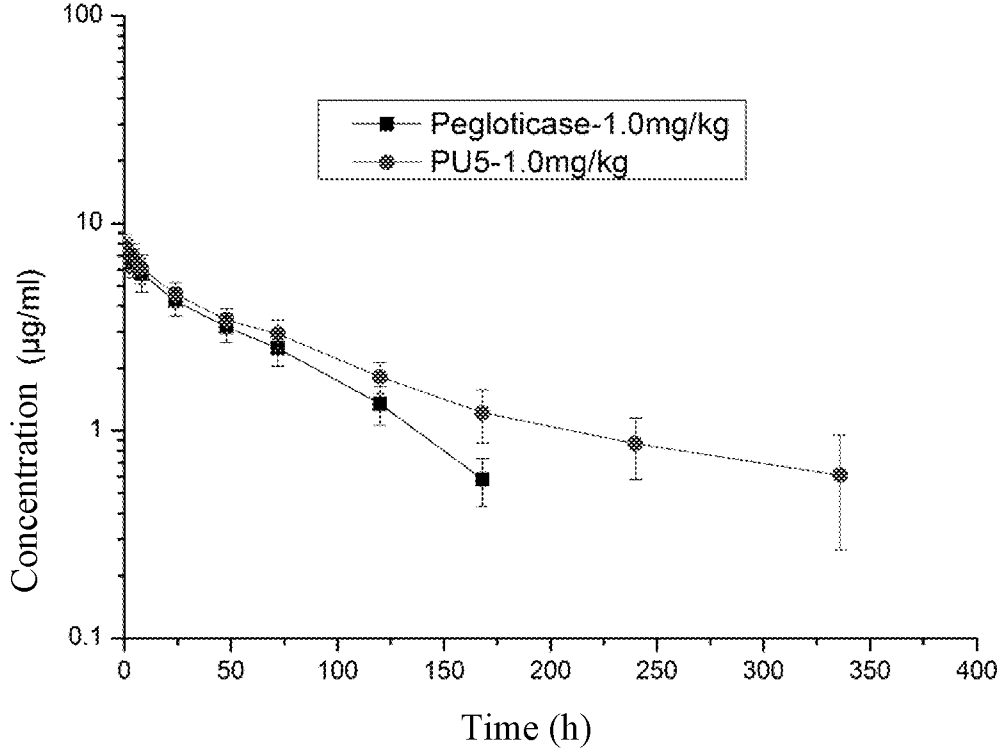
FIG. 10 is a graph illustrating mean serum drug concentration-time curve of various groups after a single intravenous injection of the same dose (1.0 mg/kg) of Pegloticase and a pegylated uricase injection in SD rats according to an embodiment of the present disclosure.
Figure 11:
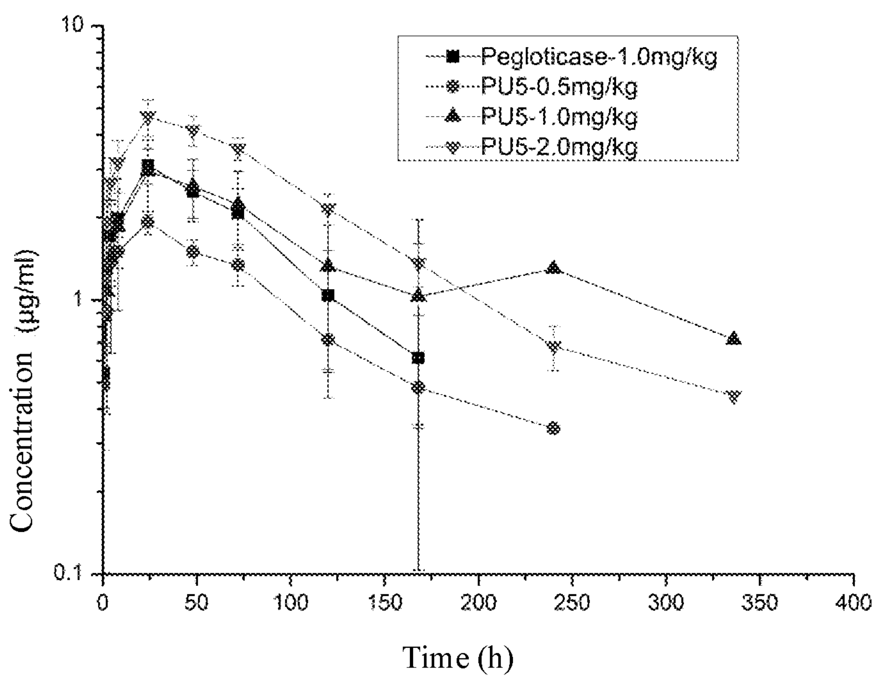
FIG. 11 illustrates mean serum drug concentration-time curves of various groups after a single intramuscular injection of Pegloticase and pegylated uricase injections of different doses in SD rats according to an embodiment of the present disclosure.
Figure 12:
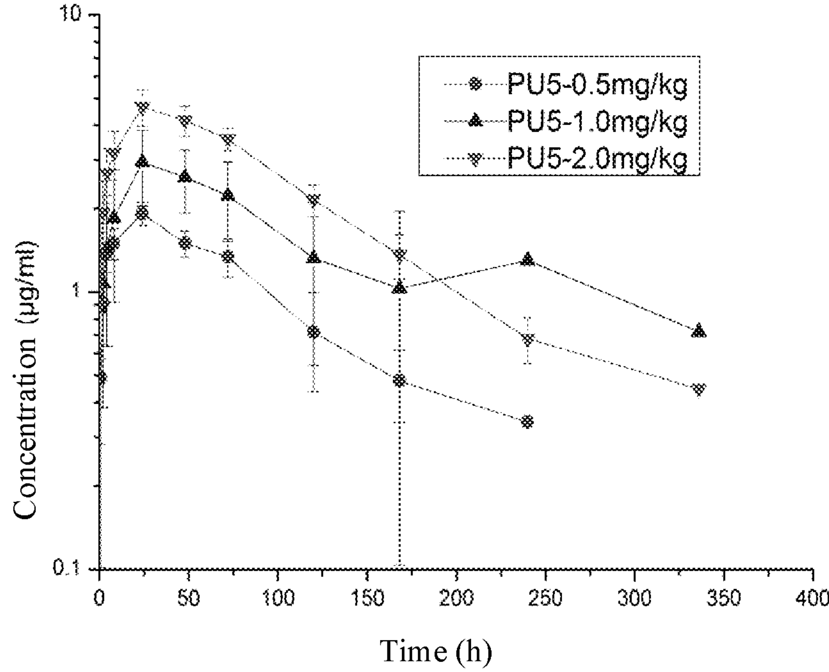
FIG. 12 illustrates mean serum drug concentration-time curves of various groups after a single intramuscular injection of pegylated uricase injections of different doses in SD rats according to an embodiment of the present disclosure.

The above pharmacokinetic results are shown in Tables 10 to 15, and FIG. 10 to FIG. 12.

TABLE 9

Animal grouping and dose design

| No | Group | Administration route | Administration frequency | Administration dose (mg/kg) | Administration concentration (mg/ml) | Administration volume (ml/kg) | Number of animals M | Number of animals F |
|---|---|---|---|---|---|---|---|---|
| 1 | Pegloticase intravenous injection group | Intravenous injection | One time | 1.0 | 0.1 | 10.0 | 3 | 3 |
| 2 | Pegloticase intramuscular injection group | Intramuscular injection | One time | 1.0 | 1.0 | 1.0 | 3 | 3 |
| 3 | PU5 intravenous injection group | Intravenous injection | One time | 1.0 | 0.1 | 10.0 | 3 | 3 |
| 4 | PU5 low-dose intramuscular injection group | Intramuscular injection | One time | 0.5 | 0.5 | 1.0 | 3 | 3 |
| 5 | PU5 medium-dose intramuscular injection group | Intramuscular injection | One time | 1.0 | 1.0 | 1.0 | 3 | 3 |
| 6 | PU5 high-dose intramuscular injection group | Intramuscular injection | One time | 2.0 | 2.0 | 1.0 | 3 | 3 |

4.2.1. Pharmacokinetic Comparison

All the SD rats, before the administration, each had a serum drug concentration level lower than the lower limit of quantification (LLOQ: 312.500 ng/mL), and after one single intramuscular injection of 0.5 mg/kg, 1.0 mg/kg, and 2.0 mg/kg of the drug, in a period from 0 h to 168 h (0 to 7 days), the serum drug concentration of the pegylated uricase injection (PU5) was dose-dependent and had an overall level increasing with the increase in the administered dose; and 168 hours later, the blood drug concentration of the pegloticase intramuscular administration group was lower than the lower limit of quantification, and the blood drug concentration of the PU5 intramuscular administration group maintained for more than 240 h.

TABLE 10

Individual blood drug concentration data and statistical analysis data when the SD rats received a single intravenous injection of 1.0 mg/kg Pegloticase (unit: μg/mL)

| Sampling | Male | | | | | | Female | | | | | | Female + Male | | |
|---|---|---|---|---|---|---|---|---|---|---|---|---|---|---|---|
| time (h) | 1M001 | 1M002 | 1M003 | N | Mean | SD | 1F001 | 1F002 | 1F003 | N | Mean | SD | N | Mean | SD |
| 0 | BLQ | BLQ | BLQ | 0 | / | / | BLQ | BLQ | BLQ | 0 | / | / | 0 | / | / |
| 0.08333 | 8.03 | 7.466 | 8.078 | 3 | 7.858 | 0.340 | 6.495 | 6.402 | 7.828 | 3 | 6.908 | 0.798 | 6 | 7.383 | 0.756 |
| 0.5 | 8.042 | 7.352 | 7.926 | 3 | 7.773 | 0.369 | 6.257 | 6.141 | 7.618 | 3 | 6.672 | 0.821 | 6 | 7.223 | 0.830 |
| 2 | 5.917 | 7.235 | 6.914 | 3 | 6.689 | 0.687 | 6.056 | 5.875 | 6.836 | 3 | 6.256 | 0.511 | 6 | 6.472 | 0.591 |
| 4 | 7.598 | 7.047 | 6.757 | 3 | 7.134 | 0.427 | 5.595 | 4.922 | 7.164 | 3 | 5.894 | 1.150 | 6 | 6.514 | 1.031 |
| 8 | 7.144 | 5.852 | 6.492 | 3 | 6.496 | 0.646 | 5.005 | 4.121 | 5.748 | 3 | 4.958 | 0.815 | 6 | 5.727 | 1.069 |
| 24 | 4.992 | 3.923 | 4.469 | 3 | 4.461 | 0.535 | 3.764 | 3.341 | 4.862 | 3 | 3.989 | 0.785 | 6 | 4.225 | 0.654 |
| 48 | 3.552 | 2.934 | 3.304 | 3 | 3.263 | 0.311 | 2.988 | 2.415 | 3.836 | 3 | 3.080 | 0.715 | 6 | 3.172 | 0.503 |
| 72 | 3.009 | 2.271 | 2.422 | 3 | 2.567 | 0.390 | 2.223 | 1.994 | 3.103 | 3 | 2.440 | 0.585 | 6 | 2.504 | 0.450 |
| 120 | 1.522 | 1.483 | 1.246 | 3 | 1.417 | 0.149 | 0.985 | 1.098 | 1.734 | 3 | 1.272 | 0.404 | 6 | 1.345 | 0.284 |
| 168 | 0.652 | 0.629 | 0.316 | 3 | 0.532 | 0.188 | 0.497 | 0.672 | 0.726 | 3 | 0.632 | 0.120 | 6 | 0.582 | 0.151 |
| 240 | BLQ | BLQ | BLQ | 0 | / | / | BLQ | BLQ | BLQ | 0 | / | / | 0 | / | / |
| 336 | BLQ | BLQ | BLQ | 0 | / | / | BLQ | BLQ | BLQ | 0 | / | / | 0 | / | / |

Notes:
"/" means no relevant information.

TABLE 11

Individual blood drug concentration data and statistical analysis data when the SD rats received a single intravenous injection of 1.0 mg/kg pegylated uricase (unit: μg/mL)

| Sampling | Male | | | | | | Female | | | | | | Female + Male | | |
|---|---|---|---|---|---|---|---|---|---|---|---|---|---|---|---|
| time (h) | 3M001 | 3M002 | 3M003 | N | Mean | SD | 3F001 | 3F002 | 3F003 | N | Mean | SD | N | Mean | SD |
| 0 | BLQ | BLQ | BLQ | 0 | / | / | BLQ | BLQ | BLQ | 0 | / | / | 0 | / | / |
| 0.08333 | 7.364 | 9.941 | 7.74 | 3 | 8.348 | 1.392 | 7.236 | 5.991 | 6.657 | 3 | 6.628 | 0.623 | 6 | 7.488 | 1.348 |
| 0.5 | 7.316 | 9.469 | 7.693 | 3 | 8.159 | 1.150 | 7.051 | 5.513 | 6.36 | 3 | 6.308 | 0.770 | 6 | 7.234 | 1.340 |
| 2 | 7.742 | 9.084 | 7.338 | 3 | 8.055 | 0.914 | 6.063 | 5.522 | 6.44 | 3 | 6.008 | 0.461 | 6 | 7.032 | 1.294 |
| 4 | 7 | 8.837 | 6.997 | 3 | 7.611 | 1.061 | 6.508 | 5.735 | 6.288 | 3 | 6.177 | 0.398 | 6 | 6.894 | 1.064 |
| 8 | 6.628 | 7.43 | 6.61 | 3 | 6.889 | 0.468 | 5.387 | 4.85 | 5.52 | 3 | 5.252 | 0.355 | 6 | 6.071 | 0.971 |
| 24 | 4.672 | 5.628 | 4.746 | 3 | 5.015 | 0.532 | 4.291 | 3.919 | 4.129 | 3 | 4.113 | 0.187 | 6 | 4.564 | 0.609 |
| 48 | 3.307 | 4.264 | 3.497 | 3 | 3.689 | 0.507 | 3.406 | 3.042 | 3.014 | 3 | 3.154 | 0.219 | 6 | 3.422 | 0.456 |
| 72 | 2.933 | 3.762 | 3.124 | 3 | 3.273 | 0.434 | 2.859 | 2.596 | 2.319 | 3 | 2.591 | 0.270 | 6 | 2.932 | 0.494 |
| 120 | 1.986 | 2.279 | 1.989 | 3 | 2.085 | 0.168 | 1.604 | 1.617 | 1.454 | 3 | 1.558 | 0.091 | 6 | 1.822 | 0.313 |
| 168 | 1.268 | 1.742 | 1.391 | 3 | 1.467 | 0.246 | 1.187 | 1.031 | 0.699 | 3 | 0.972 | 0.249 | 6 | 1.220 | 0.350 |
| 240 | 0.67 | 1.19 | 0.734 | 3 | 0.865 | 0.284 | BLQ | BLQ | BLQ | 0 | / | / | 3 | 0.865 | 0.284 |
| 336 | BLQ | 0.853 | 0.368 | 2 | 0.611 | 0.343 | BLQ | BLQ | BLQ | 0 | / | / | 2 | 0.611 | 0.343 |

Notes:
"/" means no relevant information.

TABLE 12

Individual blood drug concentration data and statistical analysis data when the SD rats received a single intramuscular injection of 1.0 mg/kg Pegloticase (unit: μg/mL)

| Sampling | Male | | | | | | Female | | | | | | Female + Male | | |
|---|---|---|---|---|---|---|---|---|---|---|---|---|---|---|---|
| time (h) | 2M001 | 2M002 | 2M003 | N | Mean | SD | 2F001 | 2F002 | 2F003 | N | Mean | SD | N | Mean | SD |
| 0 | BLQ | BLQ | BLQ | 0 | / | / | BLQ | BLQ | BLQ | 0 | / | / | 0 | / | / |
| 0.5 | 0.652 | BLQ | 0.581 | 2 | 0.617 | 0.050 | 0.388 | BLQ | BLQ | 1 | 0.388 | / | 3 | 0.540 | 0.137 |
| 2 | 1.337 | 1.249 | 1.62 | 3 | 1.402 | 0.194 | 1.172 | 1.135 | BLQ | 2 | 1.154 | 0.026 | 5 | 1.303 | 0.194 |
| 4 | 2.298 | 1.699 | 2.348 | 3 | 2.115 | 0.361 | 1.812 | 1.371 | 0.773 | 3 | 1.319 | 0.521 | 6 | 1.717 | 0.593 |
| 8 | 2.56 | 2.058 | 2.396 | 3 | 2.338 | 0.256 | 1.915 | 1.657 | 1.273 | 3 | 1.615 | 0.323 | 6 | 1.977 | 0.474 |
| 24 | 3.808 | 3.235 | 3.309 | 3 | 3.451 | 0.312 | 2.947 | 2.808 | 2.493 | 3 | 2.749 | 0.233 | 6 | 3.100 | 0.456 |
| 48 | 3.188 | 2.618 | 2.749 | 3 | 2.852 | 0.299 | 2.317 | 2.279 | 1.729 | 3 | 2.108 | 0.329 | 6 | 2.480 | 0.495 |
| 72 | 2.694 | 2.263 | 2.211 | 3 | 2.389 | 0.265 | 1.984 | 2.016 | 1.261 | 3 | 1.754 | 0.427 | 6 | 2.072 | 0.471 |
| 120 | 1.56 | 1.169 | 1.332 | 3 | 1.354 | 0.196 | 0.884 | 1.111 | 0.174 | 3 | 0.723 | 0.489 | 6 | 1.038 | 0.480 |
| 168 | BLQ | 0.341 | 0.869 | 2 | 0.605 | 0.373 | BLQ | 0.635 | BLQ | 1 | 0.635 | / | 3 | 0.615 | 0.265 |

TABLE 12-continued

Individual blood drug concentration data and statistical analysis data when the SD rats received a single intramuscular injection of 1.0 mg/kg Pegloticase (unit: μg/mL)

| Sampling | Male | | | | | | Female | | | | | | Female + Male | | |
|---|---|---|---|---|---|---|---|---|---|---|---|---|---|---|---|
| time (h) | 2M001 | 2M002 | 2M003 | N | Mean | SD | 2F001 | 2F002 | 2F003 | N | Mean | SD | N | Mean | SD |
| 240 | BLQ | BLQ | BLQ | 0 | / | / | BLQ | BLQ | BLQ | 0 | / | / | 0 | / | / |
| 336 | BLQ | BLQ | BLQ | 0 | / | / | BLQ | BLQ | BLQ | 0 | / | / | 0 | / | / |

Note:
"/" means no relevant information.

TABLE 13

Individual blood drug concentration data and statistical analysis data when the SD rats received a single intramuscular injection of 1.0 mg/kg pegylated uricase (unit: μg/mL)

| Sampling | Male | | | | | | Female | | | | | | Female + Male | | |
|---|---|---|---|---|---|---|---|---|---|---|---|---|---|---|---|
| time (h) | 5M001 | 5M002 | 5M003 | N | Mean | SD | 5F001 | 5F002 | 5F003 | N | Mean | SD | N | Mean | SD |
| 0 | BLQ | BLQ | BLQ | 0 | / | / | BLQ | BLQ | BLQ | 0 | / | / | 0 | / | / |
| 0.5 | BLQ | 1.421 | 0.328 | 2 | 0.875 | 0.773 | BLQ | BLQ | BLQ | 0 | / | / | 2 | 0.875 | 0.773 |
| 2 | BLQ | 2.295 | 0.923 | 2 | 1.609 | 0.970 | 0.593 | 0.905 | 0.674 | 3 | 0.724 | 0.162 | 5 | 1.078 | 0.695 |
| 4 | 0.729 | 2.897 | 1.648 | 3 | 1.758 | 1.088 | 1.356 | 1.222 | 0.762 | 3 | 1.113 | 0.312 | 6 | 1.436 | 0.798 |
| 8 | 1.305 | 3.628 | 2.054 | 3 | 2.329 | 1.186 | 1.559 | 1.249 | 1.266 | 3 | 1.358 | 0.174 | 6 | 1.844 | 0.926 |
| 24 | 2.408 | 4.617 | 3.069 | 3 | 3.365 | 1.134 | 3.01 | 2.339 | 2.216 | 3 | 2.522 | 0.427 | 6 | 2.943 | 0.895 |
| 48 | 2.068 | 3.877 | 2.4 | 3 | 2.782 | 0.963 | 2.739 | 2.298 | 2.189 | 3 | 2.409 | 0.291 | 6 | 2.595 | 0.668 |
| 72 | 1.76 | 3.606 | 2.027 | 3 | 2.464 | 0.998 | 2.385 | 1.761 | 1.863 | 3 | 2.003 | 0.335 | 6 | 2.234 | 0.712 |
| 120 | 1.042 | 2.9 | 1.107 | 3 | 1.683 | 1.054 | 1.169 | 0.811 | 0.926 | 3 | 0.969 | 0.183 | 6 | 1.326 | 0.782 |
| 168 | 0.479 | 2.419 | 0.631 | 3 | 1.176 | 1.079 | 0.595 | BLQ | BLQ | 1 | 0.595 | / | 4 | 1.031 | 0.928 |

TABLE 14

Average pharmacokinetic parameters of SD rats after a single intravenous injection of Pegloticase and pegylated uricase injections

| Dose (mg/kg) | Gender | Parameter | $t_{1/2}$ (h) | $C_{5\ min}$ (μg/mL) | $AUC_{last}$ (h * /mL) | $AUC_{0-\infty}$ (h * μg/mL) | $V_z$ (mL/kg) | Cl (mL/h/kg) | $MRT_{last}$ (h) |
|---|---|---|---|---|---|---|---|---|---|
| 1.0 (Pegloticase) | Male | N | 3 | 3 | 3 | 3 | 3 | 3 | 3 |
| | | Mean | 45.70 | 7.86 | 448.57 | 484.58 | 136.90 | 2.08 | 52.36 |
| | | SD | 7.57 | 0.34 | 42.16 | 46.96 | 26.57 | 0.19 | 2.58 |
| | Female | N | 3 | 3 | 3 | 3 | 3 | 3 | 3 |
| | | Mean | 53.32 | 6.91 | 404.38 | 453.63 | 173.91 | 2.26 | 54.64 |
| | | SD | 7.98 | 0.80 | 86.21 | 90.21 | 43.64 | 0.40 | 2.62 |
| | Female + Male | N | 6 | 6 | 6 | 6 | 6 | 6 | 6 |
| | | Mean | 49.51 | 7.39 | 426.48 | 469.11 | 155.40 | 2.17 | 53.50 |
| | | SD | 8.12 | 0.76 | 65.34 | 66.52 | 38.14 | 0.30 | 2.64 |
| 1.0 (PU5) | Male | N | 3 | 3 | 3 | 3 | 3 | 3 | 3 |
| | | Mean | 105.16 | 8.35 | 692.29 | 794.77 | 186.76 | 1.31 | 90.87 |
| | | SD | 41.08 | 1.39 | 128.22 | 197.50 | 24.94 | 0.29 | 14.06 |
| | Female | N | 3 | 3 | 3 | 3 | 3 | 3 | 3 |
| | | Mean | 67.09 | 6.63 | 438.93 | 535.17 | 180.63 | 1.88 | 58.58 |
| | | SD | 9.24 | 0.62 | 26.51 | 59.13 | 11.64 | 0.21 | 2.76 |
| | Female + Male | N | 6 | 6 | 6 | 6 | 6 | 6 | 6 |
| | | Mean | 86.12 | 7.49 | 565.61 | 664.97 | 183.70 | 1.59 | 74.73 |
| | | SD | 33.82 | 1.35 | 161.60 | 192.92 | 17.73 | 0.39 | 19.87 |

TABLE 15

Average pharmacokinetic parameters of SD rats after a single intramuscular injection of Peglocticase and pegylated uricase injections

| Dose (mg/kg) | Gender | Parameter | $t_{1/2}$ (h) | $T_{max}$ (h) | $C_{max}$ (μg/mL) | $AUC_{last}$ (h * μg/mL) | $AUC_{0-\infty}$ (h * μg/mL) | Vz_F (mL/kg) | Cl_F (mL/h/kg) | $MRT_{last}$ (h) |
|---|---|---|---|---|---|---|---|---|---|---|
| 1.0 (Pegloticase) | Male | N | 3 | 3 | 3 | 3 | 3 | 3 | 3 | 3 |
| | | Mean | 58.31 | 24.00 | 3.45 | 318.23 | 405.13 | 203.75 | 2.54 | 60.57 |
| | | SD | 20.10 | 0.00 | 0.31 | 15.37 | 80.13 | 42.90 | 0.54 | 6.54 |
| | Female | N | 3 | 3 | 3 | 3 | 3 | 3 | 3 | 3 |
| | | Mean | 52.12 | 24.00 | 2.75 | 210.14 | 278.56 | 276.83 | 3.72 | 51.27 |
| | | SD | 4.78 | 0.00 | 0.23 | 79.35 | 60.90 | 50.57 | 0.91 | 15.28 |
| | Female + Male | N | 6 | 6 | 6 | 6 | 6 | 6 | 6 | 6 |
| | | Mean | 55.21 | 24.00 | 3.10 | 264.19 | 341.85 | 240.29 | 3.13 | 55.92 |
| | | SD | 13.50 | 0.00 | 0.46 | 78.22 | 94.12 | 57.97 | 0.93 | 11.68 |
| 0.5 (PU5) | Male | N | 3 | 3 | 3 | 3 | 3 | 3 | 3 | 3 |
| | | Mean | 63.57 | 24.00 | 1.93 | 181.10 | 233.11 | 199.06 | 2.21 | 60.26 |
| | | SD | 18.68 | 0.00 | 0.26 | 79.19 | 48.71 | 56.50 | 0.45 | 23.89 |
| | Female | N | 3 | 3 | 3 | 3 | 3 | 3 | 3 | 3 |
| | | Mean | 48.20 | 24.00 | 1.91 | 170.63 | 205.87 | 167.09 | 2.56 | 55.67 |
| | | SD | 17.38 | 0.00 | 0.14 | 41.99 | 61.41 | 21.47 | 0.67 | 11.48 |
| | Female + Male | N | 6 | 6 | 6 | 6 | 6 | 6 | 6 | 6 |
| | | Mean | 55.88 | 24.00 | 1.92 | 175.87 | 219.49 | 183.07 | 2.38 | 57.97 |
| | | SD | 18.20 | 0.00 | 0.19 | 56.98 | 51.77 | 42.05 | 0.54 | 16.95 |
| 1.0 (PU5) | Male | N | 3 | 3 | 3 | 3 | 3 | 3 | 3 | 3 |
| | | Mean | 70.47 | 24.00 | 3.36 | 439.83 | 504.61 | 225.86 | 2.57 | 84.20 |
| | | SD | 28.55 | 0.00 | 1.13 | 307.66 | 344.91 | 54.21 | 1.32 | 31.10 |
| | Female | N | 3 | 3 | 3 | 3 | 3 | 3 | 3 | 3 |
| | | Mean | 50.44 | 24.00 | 2.52 | 235.90 | 293.04 | 252.46 | 3.46 | 58.28 |
| | | SD | 5.05 | 0.00 | 0.43 | 58.01 | 45.24 | 46.82 | 0.50 | 6.96 |
| | Female + Male | N | 6 | 6 | 6 | 6 | 6 | 6 | 6 | 6 |
| | | Mean | 60.45 | 24.00 | 2.94 | 337.86 | 398.83 | 239.16 | 3.02 | 71.24 |
| | | SD | 21.37 | 0.00 | 0.89 | 227.34 | 248.66 | 47.59 | 1.02 | 24.65 |
| 2.0 (PU5) | Male | N | 3 | 3 | 3 | 3 | 3 | 3 | 3 | 3 |
| | | Mean | 66.65 | 24.00 | 4.84 | 590.58 | 649.31 | 292.61 | 3.10 | 85.42 |
| | | SD | 20.11 | 0.00 | 0.46 | 59.68 | 55.26 | 64.39 | 0.27 | 19.91 |
| | Female | N | 3 | 3 | 3 | 3 | 3 | 3 | 3 | 3 |
| | | Mean | 72.51 | 32.00 | 4.55 | 537.05 | 628.72 | 339.98 | 3.22 | 79.26 |
| | | SD | 15.56 | 13.86 | 0.91 | 124.85 | 78.17 | 100.19 | 0.42 | 9.60 |
| | Female + Male | N | 6 | 6 | 6 | 6 | 6 | 6 | 6 | 6 |
| | | Mean | 69.58 | 28.00 | 4.70 | 563.81 | 639.01 | 316.30 | 3.16 | 82.34 |
| | | SD | 16.40 | 9.80 | 0.66 | 92.30 | 61.59 | 79.67 | 0.32 | 14.38 |

4.2.2. Comparison of In Vivo Efficacy (Uric Acid)

Figure 13:
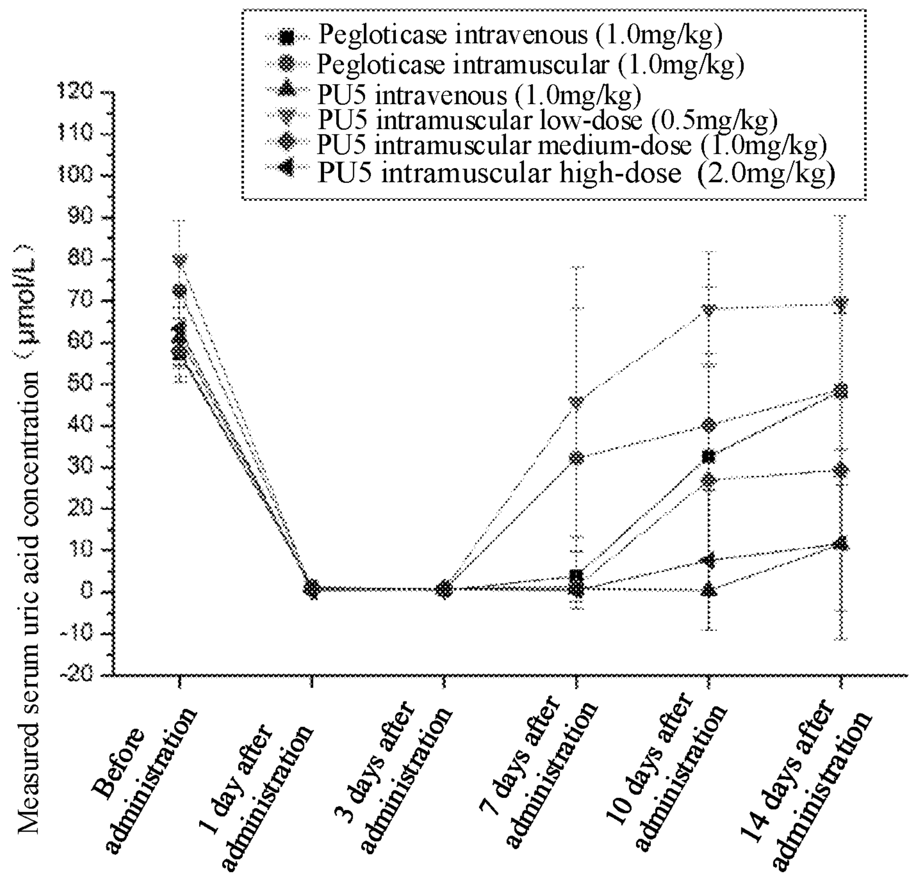
FIG. 13 illustrates mean serum uric acid value-time curves of various groups after a single intramuscular/intravenous injection of Pegloticase and pegylated uricase injections of different doses in SD rats according to an embodiment of the present disclosure.
Figure 14:
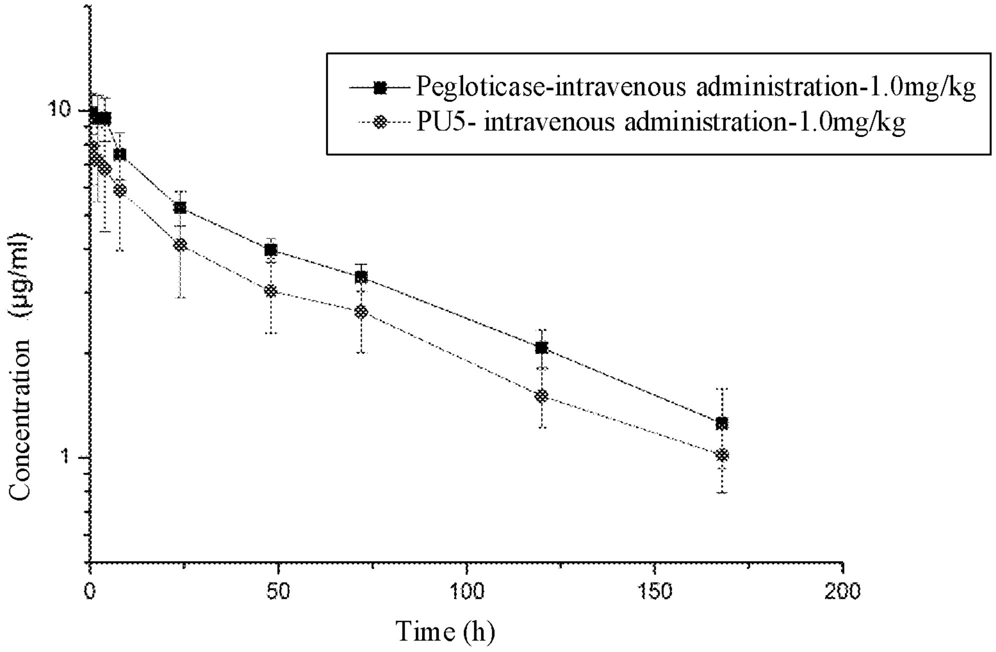
FIG. 14 illustrates mean serum drug concentration-time curves of male and female SD rats after the first intravenous injection (Day 1) of the same dose (1.0 mg/kg) of Pegloticase and a pegylated uricase injection according to an embodiment of the present disclosure.
Figure 15:
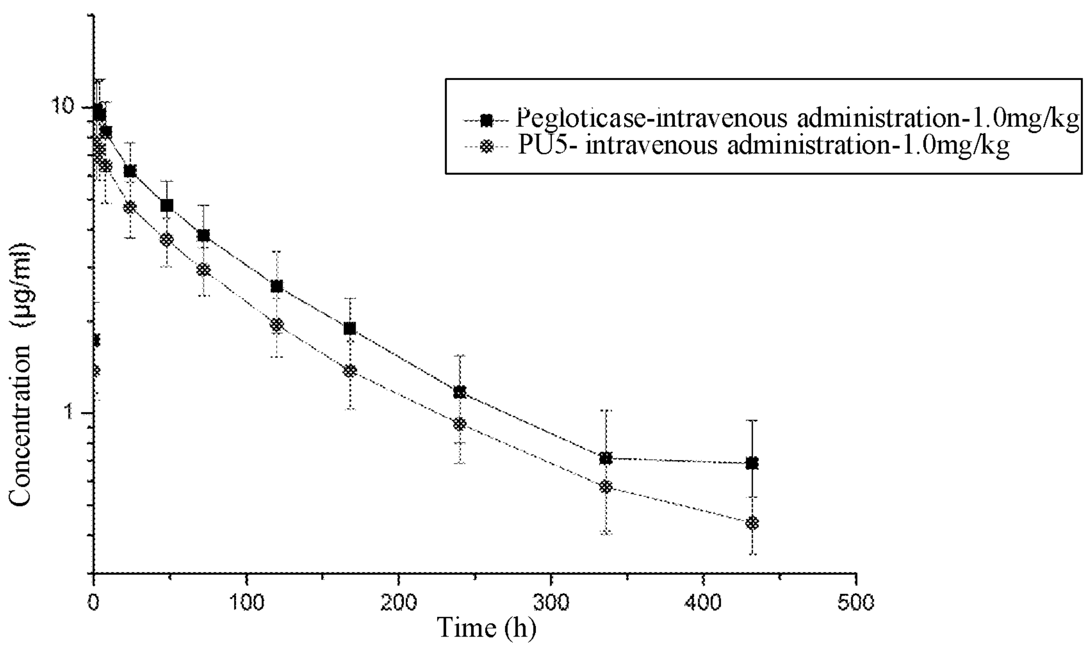
FIG. 15 illustrates mean serum drug concentration-time curves of male and female SD rats after the last intravenous injection (Day 22) of the same dose (1.0 mg/kg) of Pegloticase and a pegylated uricase injection according to an embodiment of the present disclosure.
Figure 16:
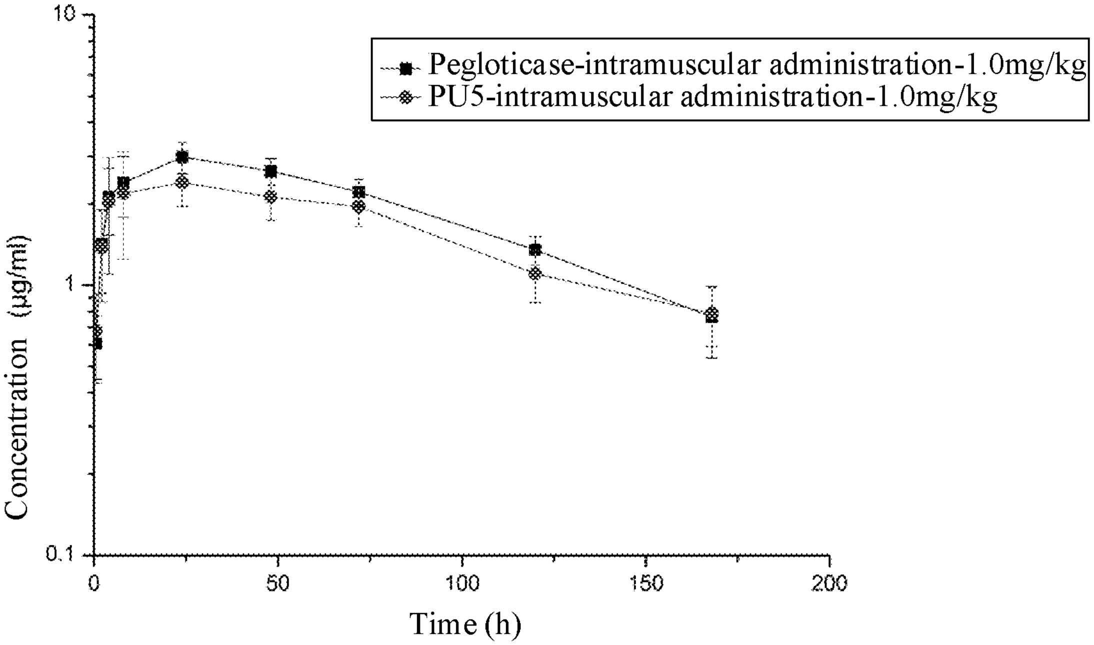
FIG. 16 illustrates mean serum drug concentration-time curves of male and female SD rats after the first intramuscular injection (Day 1) of the same dose (1.0 mg/kg) of Pegloticase and a pegylated uricase injection according to an embodiment of the present disclosure.
Figure 17:
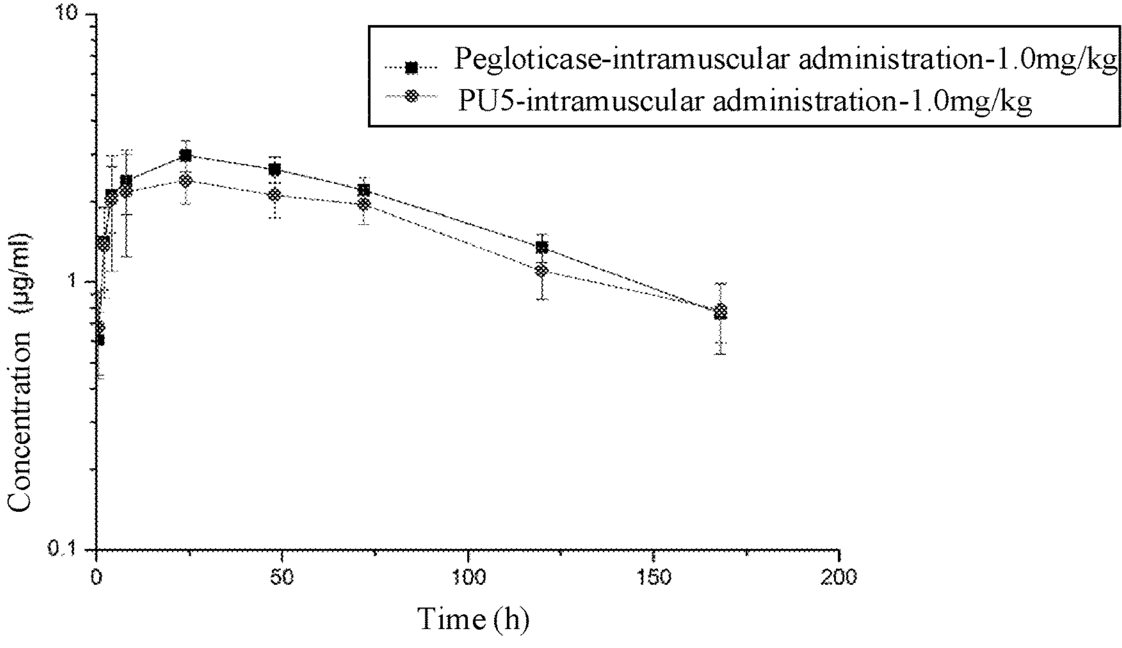
FIG. 17 illustrates mean serum drug concentration-time curves of male and female SD rats after the last intramuscular injection (Day 22) of the same dose (1.0 mg/kg) of Pegloticase and a pegylated uricase injection according to an embodiment of the present disclosure.
Figure 18:
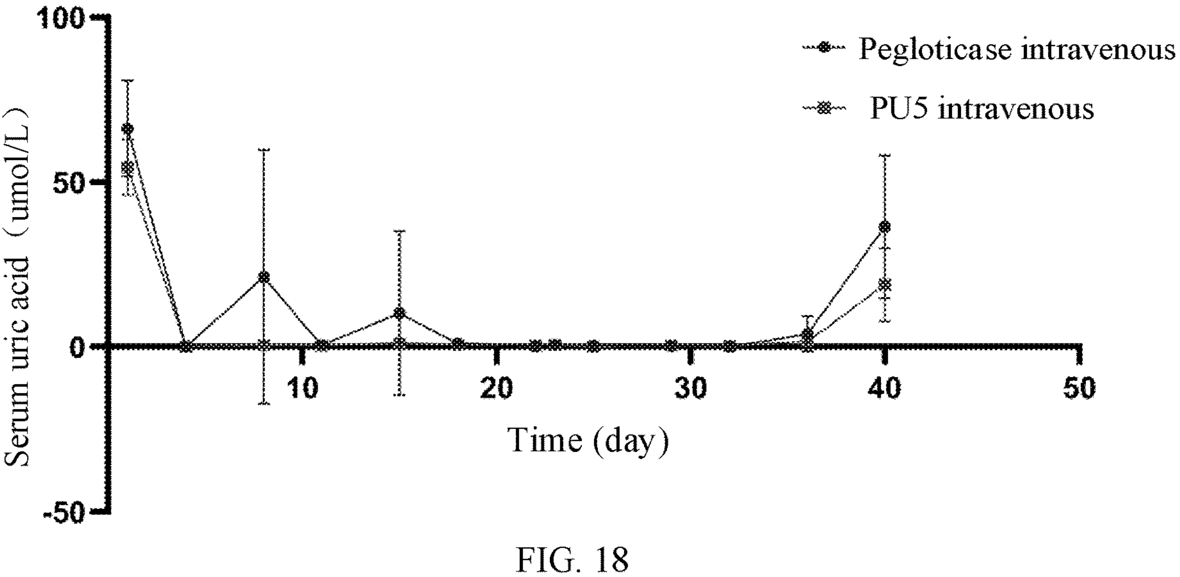
FIG. 18 illustrates mean serum uric acid value-time curves after multiple intravenous injections of Pegloticase and a pegylated uricase injection in SD rats according to an embodiment of the present disclosure.
Figure 19:
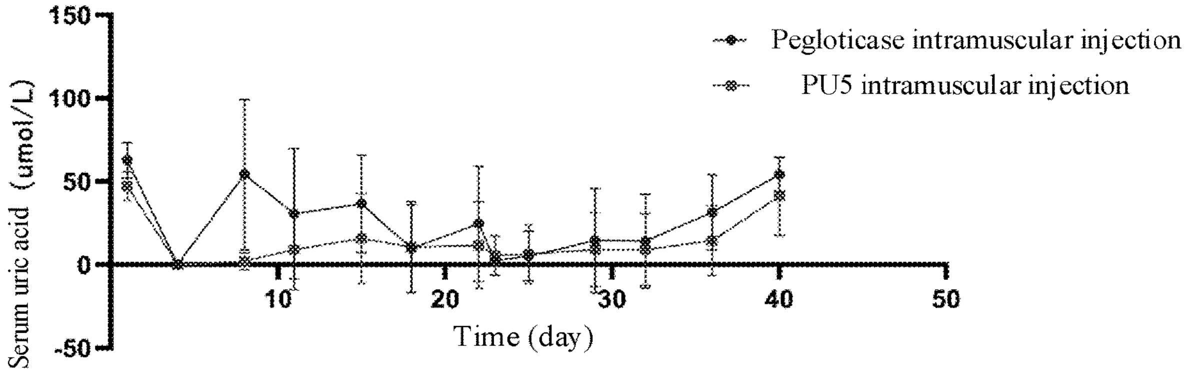
FIG. 19 illustrates mean serum uric acid value-time curves after multiple intramuscular injections of Pegloticase and a pegylated uricase injection in SD rats according to an embodiment of the present disclosure.

After a single intramuscular injection of 0.5 mg/kg, 1.0 mg/kg, 2.0 mg/kg pegylated uricase injection, the uric acid concentration maintained at a low level 1 day and 3 days after the administration, the uric acid level of each dose group began to recover 7 days after the administration, and the higher the dose, the longer the uric acid maintained a lower level in the body. Comparing the intravenous injection groups of the same dose, the PU5 intravenous injection group maintained a low concentration level of serum uric acid for a longer time than the pegloticase intravenous injection group. Comparing the intramuscular injection groups of the same dose, the PU5 intramuscular injection group maintained a low concentration level of serum uric acid for a longer time than the pegloticase intramuscular injection group. Comparing the groups of the same dose, the PU5 intravenous or intramuscular injection group maintained a low concentration level of serum uric acid for a longer time than the pegloticase intravenous or intramuscular injection group, that is, PU5 maintained a low concentration level of uric acid in the body for a longer time than pegloticase in each case. The results are illustrated in FIG. 13.

4.3 Evaluation of Multiple Administrations of Polyethylene Glycol-Modified Urate Oxidase in Rats In this experiment, 4 groups were set, i.e., a marketed drug Pegloticase intravenous injection group, a Pegloticase intramuscular injection group, a pegylated uricase (PU5) intravenous injection group, and a PU5 intramuscular injection group, each group included 8 rats, four of which were male and the other four of which were female, 32 SD rats in total. The Pegloticase and pegylated uricase intravenous injection groups adopted intravenous injection; and the Pegloticase and pegylated uricase intramuscular injection groups adopted intramuscular injection. The administration dose was 1.0 mg/kg, once a week, for 4 consecutive times.

The result analysis indicates that:

SD rats were injected intravenously/intramuscularly with 1.0 mg/kg Pegloticase and pegloticase injections for multiple times, The general condition of the rats had no abnormal changes related to the drugs.

4.3.1 Anti-PEG Antibody Detection

SD rats were administrated for 4 consecutive times. Before the first administration, no anti-PEG antibodies and no anti-PHC antibodies were detected in either individual animal; after the administration, no anti-PHC antibodies were detected in either animal, anti-PEG antibodies were detected in each group of the Pegloticase intravenous and intramuscular injection groups as well as the pegylated uricase intravenous and intramuscular injection groups, and the ratios of positive results were: 3/8, 1/8, 1/8, and 1/8, respectively. The PEG immunohistochemical examination revealed that the spleen, liver and kidney of the pegloticase intravenous and intramuscular injection groups showed weak positive expression of PEG; and no positive expression of PEG was found in the pegylated uricase intravenous and intramuscular injection groups. The results are shown in Table 16.

From the above analysis, it can be seen that the antibodies induced by PU5 and pegloticase are mainly antibodies against the PEG part, rather than antibodies against the urate oxidase part.

According to the results of PEG antibody and PEG immunohistochemistry, the intramuscular administration groups of both PU5 and pegloticase are superior to the intravenous administration groups thereof. Among them, regarding the produced anti-PEG antibodies of the intravenous administration groups, PU5 is superior to pegloticase; and regarding the produced anti-PEG antibodies of the intramuscular administration groups, PU5 is superior to pegloticase.

4.3.2 Pharmacokinetic Tests

The SD rats that had received multiple intravenous and intramuscular injections of Pegloticase and pegylated uricase injections exhibited no significant gender difference in the main pharmacokinetic parameters between the groups. After 4 consecutive administrations, these two drugs accumulated slightly in rats.

When the SD rats received multiple intravenous/intramuscular injection administrations with the same dose (1.0 mg/kg) of the marketed drug Pegloticase, the absolute bioavailability in the rats was 51.35% after the first administration; and the absolute bioavailability in the rats was 45.98% after the last administration. When the SD rats received multiple intravenous/intramuscular injection administrations with the same dose (1.0 mg/kg) of the pegylated uricase injection, the absolute bioavailability in the rats was 58.29% after the first administration; and the absolute bioavailability in the rats was 52.60% after the last administration.

4.3.3 Comparison of In Vivo Drug Efficacy (Uric Acid)

SD rats were injected intravenously and intramuscularly with 1.0 mg/kg Pegloticase and 1.0 mg/kg pegylated uricase injection for 4 consecutive times (1 time/week), the serum uric acid concentration maintained at a low level after each administration; the serum uric acid concentration recovered 14 days after the last administration in the Pegloticase intramuscular injection group, and in the rest groups, the serum uric acid concentration recovered 18 days after the last administration. Compared with the same dose of the

TABLE 16

PEG immunohistochemistry positive expression results

| Microscopic observation | | Incidence: Pegloticase intravenous injection group | | Pegloticase intramuscular injection Group | | PU5 intravenous injection group | | PU5 intramuscular injection group | |
|---|---|---|---|---|---|---|---|---|---|
| | | Male | Female | Male | Female | Male | Female | Male | Female |
| Spleen | Total inspection number: | 4 | 4 | 4 | 4 | 4 | 4 | 4 | 4 |
| PEG, white pulp | 1 | 0 | 1 | 1 | 2 | 0 | 0 | 0 | 0 |
| | Total incidence number: | 0 | 1 | 1 | 2 | 0 | 0 | 0 | 0 |
| PEG, red pulp | 1 | 0 | 1 | 0 | 0 | 0 | 0 | 0 | 0 |
| | Total incidence number: | 0 | 1 | 0 | 0 | 0 | 0 | 0 | 0 |
| Liver | Total inspection number: | 4 | 4 | 4 | 4 | 4 | 4 | 4 | 4 |
| PEG, vascular endothelial cells/ | 1 | 4 | 4 | 1 | 3 | 0 | 0 | 0 | 0 |
| Kupffer cells | Total incidence number: | 4 | 4 | 1 | 3 | 0 | 0 | 0 | 0 |
| Kidney | Total inspection number: | 4 | 4 | 4 | 4 | 4 | 4 | 4 | 4 |
| PEG, renal tubules | 1 | 3 | 1 | 1 | 1 | 0 | 0 | 0 | 0 |
| | Total incidence number: | 3 | 1 | 1 | 1 | 0 | 0 | 0 | 0 |
| PEG, vascular endothelial cells | 1 | 0 | 1 | 0 | 0 | 0 | 0 | 0 | 0 |
| | Total incidence number: | 0 | 1 | 0 | 0 | 0 | 0 | 0 | 0 |

Positive grading: 1 = extremely weakly positive, 2 = weakly positive, 3 = moderately positive, 4 = strongly positive.

marketed drug Pegloticase, the maintaining time in the intravenous injection groups of these two drugs was basically consistent, and the maintaining time of the pegylated uricase intramuscular injection group was longer than that of the marketed drug intramuscular injection group. That is, for the intramuscular administration, the efficacy of PU5 is superior than that of Pegloticase.

The above results are shown in Table 17 to Table 20, and FIG. 14 to FIG. 19.

TABLE 17

Results of average pharmacokinetic parameters after continuous intravenous injection of Pegloticase and a pegylated uricase injection in SD rats

| Experiment time | Dose Drug name | Gender | Parameter | $t_{1/2}$ (h) | $T_{max}$ (h) | $C_{max}$ (μg/mL) | $AUC_{last}$ (h * μg/mL) | $AUC_{0-\infty}$ (h * μg/mL) | Vz (mL/kg) | Cl (mL/h/kg) | $MRT_{last}$ (h) |
|---|---|---|---|---|---|---|---|---|---|---|---|
| Day 1 | 1.0 mg/kg Pegloticase | Male | N | 4 | 4 | 4 | 4 | 4 | 4 | 4 | 4 |
| | | | Mean | 72.17 | 2.13 | 11.12 | 632.58 | 778.65 | 133.74 | 1.29 | 56.91 |
| | | | SD | 4.53 | 1.44 | 0.28 | 25.32 | 45.00 | 4.49 | 0.07 | 1.17 |
| | | Female | N | 4 | 4 | 4 | 4 | 4 | 4 | 4 | 4 |
| | | | Mean | 66.24 | 0.50 | 8.84 | 514.21 | 633.80 | 149.07 | 1.59 | 54.93 |
| | | | SD | 17.91 | 0.00 | 1.07 | 50.98 | 64.84 | 27.23 | 0.16 | 7.58 |
| | | Female + Male | N | 8 | 8 | 8 | 8 | 8 | 8 | 8 | 8 |
| | | | Mean | 69.21 | 1.31 | 9.98 | 573.40 | 706.22 | 141.41 | 1.44 | 55.92 |
| | | | SD | 12.51 | 1.28 | 1.42 | 73.43 | 93.08 | 19.84 | 0.20 | 5.13 |
| | 1.0 mg/kg PU5 | Male | N | 4 | 4 | 4 | 4 | 4 | 4 | 4 | 4 |
| | | | Mean | 67.98 | 1.75 | 9.47 | 527.73 | 634.48 | 158.66 | 1.60 | 55.50 |
| | | | SD | 8.87 | 1.66 | 0.91 | 91.07 | 91.12 | 39.53 | 0.22 | 0.89 |
| | | Female | N | 4 | 4 | 4 | 4 | 4 | 4 | 4 | 4 |
| | | | Mean | 79.29 | 1.38 | 6.42 | 369.05 | 481.09 | 238.12 | 2.16 | 59.68 |
| | | | SD | 17.07 | 1.75 | 0.61 | 49.11 | 98.31 | 15.34 | 0.53 | 2.84 |
| | | Female + Male | N | 8 | 8 | 8 | 8 | 8 | 8 | 8 | 8 |
| | | | Mean | 73.63 | 1.56 | 7.94 | 448.39 | 557.79 | 198.39 | 1.88 | 57.59 |
| | | | SD | 13.97 | 1.59 | 1.78 | 108.54 | 120.10 | 50.74 | 0.48 | 2.96 |
| Day 22 | 1.0 mg/kg Pegloticase | Male | N | 4 | 4 | 4 | 4 | 4 | 4 | 4 | 4 |
| | | | Mean | 135.63 | 1.75 | 12.33 | 1159.18 | 1300.99 | 149.28 | 0.78 | 118.29 |
| | | | SD | 40.45 | 1.66 | 0.94 | 134.20 | 208.65 | 28.13 | 0.13 | 9.91 |
| | | Female | N | 4 | 4 | 4 | 4 | 4 | 4 | 4 | 4 |
| | | | Mean | 96.09 | 0.88 | 8.02 | 672.95 | 747.61 | 186.89 | 1.35 | 92.46 |
| | | | SD | 7.69 | 0.75 | 0.87 | 78.50 | 78.66 | 24.21 | 0.14 | 9.52 |
| | | Female + Male | N | 8 | 8 | 8 | 8 | 8 | 8 | 8 | 8 |
| | | | Mean | 115.86 | 1.31 | 10.17 | 916.07 | 1024.30 | 168.09 | 1.07 | 105.37 |
| | | | SD | 34.25 | 1.28 | 2.45 | 279.12 | 329.86 | 31.53 | 0.33 | 16.48 |
| | 1.0 mg/kg PU5 | Male | N | 4 | 4 | 4 | 4 | 4 | 4 | 4 | 4 |
| | | | Mean | 149.80 | 2.25 | 9.00 | 840.78 | 947.08 | 229.16 | 1.07 | 117.99 |
| | | | SD | 24.68 | 2.02 | 0.73 | 91.96 | 104.82 | 36.69 | 0.11 | 6.88 |
| | | Female | N | 4 | 4 | 4 | 4 | 4 | 4 | 4 | 4 |
| | | | Mean | 103.90 | 1.25 | 6.63 | 576.81 | 636.52 | 236.33 | 1.63 | 101.66 |
| | | | SD | 21.25 | 0.87 | 0.72 | 128.81 | 128.02 | 17.98 | 0.39 | 20.03 |
| | | Female + Male | N | 8 | 8 | 8 | 8 | 8 | 8 | 8 | 8 |
| | | | Mean | 126.85 | 1.75 | 7.82 | 708.79 | 791.80 | 232.75 | 1.35 | 109.82 |
| | | | SD | 32.51 | 1.54 | 1.44 | 175.05 | 198.21 | 27.02 | 0.40 | 16.38 |

TABLE 18

Results of average pharmacokinetic parameters after continuous intramuscular injection of Pegloticase and pegylated uricase injection in SD rats

| Experiment time | Dose Drug name | Gender | Parameter | $t_{1/2}$ (h) | $T_{max}$ (h) | $C_{max}$ (μg/mL) | $AUC_{last}$ (h * μg/mL) | $AUC_{0-\infty}$ (h * μg/mL) | Vz_F (mL/kg) | Cl_F (mL/h/kg) | MRT last (h) |
|---|---|---|---|---|---|---|---|---|---|---|---|
| Day 1 | 1.0 mg/kg Pegloticase | Male | N | 4 | 4 | 4 | 4 | 4 | 4 | 4 | 4 |
| | | | Mean | 59.68 | 24.00 | 3.16 | 318.22 | 395.66 | 217.53 | 2.54 | 62.05 |
| | | | SD | 13.70 | 0.00 | 0.38 | 29.92 | 29.26 | 49.49 | 0.19 | 6.59 |
| | | Female | N | 4 | 4 | 4 | 4 | 4 | 4 | 4 | 4 |
| | | | Mean | 80.53 | 24.00 | 2.80 | 270.69 | 415.60 | 282.07 | 2.48 | 57.80 |
| | | | SD | 16.48 | 0.00 | 0.36 | 66.91 | 84.31 | 37.74 | 0.52 | 6.21 |
| | | Female + Male | N | 8 | 8 | 8 | 8 | 8 | 8 | 8 | 8 |
| | | | Mean | 70.11 | 24.00 | 2.98 | 294.46 | 405.63 | 249.80 | 2.51 | 59.92 |
| | | | SD | 17.91 | 0.00 | 0.39 | 54.29 | 59.39 | 53.39 | 0.36 | 6.35 |
| | 1.0 mg/kg PU5 | Male | N | 4 | 4 | 4 | 4 | 4 | 4 | 4 | 4 |
| | | | Mean | 82.25 | 6.00 | 3.06 | 290.64 | 403.89 | 294.92 | 2.50 | 61.83 |
| | | | SD | 9.79 | 2.31 | 0.25 | 34.67 | 48.73 | 29.13 | 0.31 | 6.88 |
| | | Female | N | 4 | 4 | 4 | 4 | 4 | 4 | 4 | 4 |
| | | | Mean | 70.44 | 48.00 | 2.21 | 232.11 | 306.59 | 340.32 | 3.50 | 66.28 |
| | | | SD | 13.41 | 19.60 | 0.26 | 59.53 | 90.62 | 46.97 | 1.09 | 10.28 |

TABLE 18-continued

Results of average pharmacokinetic parameters after continuous intramuscular injection of Pegloticase and pegylated uricase injection in SD rats

| Experiment time | Dose Drug name | Gender | Parameter | $t_{1/2}$ (h) | $T_{max}$ (h) | $C_{max}$ (μg/mL) | $AUC_{last}$ (h * μg/mL) | $AUC_{0-\infty}$ (h * μg/mL) | Vz_F (mL/kg) | Cl_F (mL/h/kg) | MRT last (h) |
|---|---|---|---|---|---|---|---|---|---|---|---|
| | | Female + Male | N | 8 | 8 | 8 | 8 | 8 | 8 | 8 | 8 |
| | | | Mean | 76.34 | 27.00 | 2.63 | 261.38 | 355.24 | 317.62 | 3.00 | 64.06 |
| | | | SD | 12.57 | 25.90 | 0.51 | 54.89 | 85.10 | 43.56 | 0.91 | 8.44 |
| Day 22 | 1.0 mg/kg Pegloticase | Male | N | 3 | 4 | 4 | 4 | 3 | 3 | 3 | 4 |
| | | | Mean | 198.20 | 25.00 | 3.18 | 486.70 | 799.90 | 353.52 | 1.35 | 112.01 |
| | | | SD | 83.85 | 18.00 | 0.85 | 298.21 | 293.71 | 23.56 | 0.42 | 60.30 |
| | | Female | N | 4 | 4 | 4 | 4 | 4 | 4 | 4 | 4 |
| | | | Mean | 97.92 | 20.00 | 2.69 | 355.77 | 427.75 | 344.97 | 2.65 | 94.51 |
| | | | SD | 33.98 | 8.00 | 0.71 | 134.18 | 155.69 | 88.41 | 1.19 | 30.45 |
| | | Female + Male | N | 7 | 8 | 8 | 8 | 7 | 7 | 7 | 8 |
| | | | Mean | 140.90 | 22.50 | 2.93 | 421.23 | 587.25 | 348.64 | 2.09 | 103.26 |
| | | | SD | 76.12 | 13.17 | 0.77 | 225.23 | 283.63 | 64.14 | 1.12 | 45.20 |
| | 1.0 mg/kg PU5 | Male | N | 4 | 4 | 4 | 4 | 4 | 4 | 4 | 4 |
| | | | Mean | 140.04 | 15.00 | 2.52 | 395.82 | 478.83 | 610.95 | 9.64 | 102.76 |
| | | | SD | 90.61 | 10.52 | 1.15 | 255.45 | 300.26 | 419.13 | 16.09 | 61.50 |
| | | Female | N | 4 | 4 | 4 | 4 | 4 | 4 | 4 | 4 |
| | | | Mean | 122.51 | 30.00 | 2.41 | 349.84 | 428.61 | 416.41 | 2.82 | 103.39 |
| | | | SD | 59.33 | 12.00 | 0.50 | 178.08 | 204.30 | 72.32 | 1.36 | 44.91 |
| | | Female + Male | N | 8 | 8 | 8 | 8 | 8 | 8 | 8 | 8 |
| | | | Mean | 131.27 | 22.50 | 2.46 | 372.83 | 453.72 | 513.68 | 6.23 | 103.08 |
| | | | SD | 71.52 | 13.17 | 0.82 | 205.33 | 239.26 | 297.23 | 11.18 | 49.85 |

TABLE 19

Statistical results of uric acid in each dose group after multiple intramuscular/intravenous injections of Pegloticase and a pegylated uricase injection in SD rats (Mean ± SD)

| Gender | 1.0 mg/kg Pegloticase Intravenous injection group | | 1.0 mg/kg Pegloticase Intramuscular injection group | | 1.0 mg/kg PU5 Intravenous injection group | | 1.0 mg/kg PU5 Intramuscular injection group | |
|---|---|---|---|---|---|---|---|---|
| Detection time | n | $\overline{X}$ ± SD | n | $\overline{X}$ ± SD | n | $\overline{X}$ ± SD | n | $\overline{X}$ ± SD |
| Male | | | | | | | | |
| Before 1st administration | 4 | 71.250 ± 19.103 | 4 | 62.250 ± 5.315 | 4 | 58.750 ± 7.632 | 4 | 50.750 ± 6.850 |
| 3 days after 1st administration | 4 | 0.250 ± 0.500 | 4 | 0.500 ± 0.577 | 4 | 0 ± 0 | 4 | 0 ± 0 |
| Before 2nd administration | 4 | 0.500 ± 0.577 | 4 | 69.750 ± 46.133 | 4 | 0.500 ± 0.577 | 4 | 0.250 ± 0.500 |
| 3 days after 2nd administration | 4 | 1.000 ± 0 | 4 | 20.750 ± 40.178 | 4 | 0.500 ± 0.577 | 4 | 17.500 ± 33.670 |
| Before 3rd administration | 4 | 1.000 ± 0 | 4 | 26.500 ± 30.116 | 4 | 1.250 ± 0.957 | 4 | 18.000 ± 32.680 |
| 3 days after 3rd administration | 4 | 1.000 ± 0.816 | 4 | 19.000 ± 37.336 | 4 | 0.500 ± 0.577 | 4 | 20.500 ± 38.336 |
| Before 4th administration | 4 | 0 ± 0 | 4 | 15.500 ± 31.000 | 4 | 0.250 ± 0.500 | 4 | 19.250 ± 37.170 |
| 1 day after 4th administration | 4 | 0.750 ± 0.500 | 4 | 1.750 ± 1.500 | 4 | 0.750 ± 0.500 | 4 | 9.750 ± 16.840 |
| 3 days after 4th administration | 4 | 0.500 ± 0.577 | 4 | 10.500 ± 21.000 | 4 | 0 ± 0 | 4 | 12.750 ± 24.838 |
| 7 days after 4th administration | 4 | 0.250 ± 0.500 | 4 | 22.250 ± 44.500 | 4 | 0 ± 0 | 4 | 16.250 ± 31.837 |
| 10 days after 4th administration | 4 | 0 ± 0 | 4 | 20.000 ± 38.670 | 4 | 0.250 ± 0.500 | 4 | 16.000 ± 30.681 |
| 14 days after 4th administration | 4 | 1.250 ± 0.500 | 4 | 29.250 ± 28.123 | 4 | 2.000 ± 0.816 | 4 | 19.250 ± 30.015 |
| 18 days after 4th administration | 4 | 25.000 ± 10.296 | 4 | 53.500 ± 14.933 | 4 | 24.000 ± 13.614 | 4 | 50.000 ± 29.833 |
| Female | | | | | | | | |
| Before 1st administration | 4 | 61.250 ± 8.057 | 4 | 63.000 ± 15.470 | 4 | 50.250 ± 7.500 | 4 | 43.250 ± 9.743 |
| 3 days after 1st administration | 4 | 0 ± 0 | 4 | 0 ± 0 | 4 | 0.250 ± 0.500 | 4 | 0 ± 0 |
| Before 2nd administration | 4 | 42.000 ± 48.132 | 4 | 38.250 ± 44.507 | 4 | 0.500 ± 0.577 | 4 | 4.000 ± 7.348 |

TABLE 19-continued

Statistical results of uric acid in each dose group after multiple intramuscular/intravenous injections of Pegloticase and a pegylated uricase injection in SD rats (Mean ± SD)

| Gender | 1.0 mg/kg Pegloticase Intravenous injection group | | 1.0 mg/kg Pegloticase Intramuscular injection group | | 1.0 mg/kg PU5 Intravenous injection group | | 1.0 mg/kg PU5 Intramuscular injection group | |
|---|---|---|---|---|---|---|---|---|
| Detection time | n | $\bar{X}$ ± SD | n | $\bar{X}$ ± SD | n | $\bar{X}$ ± SD | n | $\bar{X}$ ± SD |
| 3 days after $2^{nd}$ administration | 4 | 0.250 ± 0.500 | 4 | 40.250 ± 41.080 | 4 | 0.250 ± 0.500 | 4 | 0.500 ± 0.577 |
| Before $3^{rd}$ administration | 4 | 19.500 ± 35.01 | 4 | 46.750 ± 28.547 | 4 | 1.000 ± 0.816 | 4 | 13.500 ± 25.000 |
| 3 days after $3^{rd}$ administration | 4 | 1.250 ± 0.500 | 4 | 0.500 ± 0.577 | 4 | 0.750 ± 0.500 | 4 | 0.750 ± 0.500 |
| Before $4^{th}$ administration | 4 | 0.250 ± 0.500 | 4 | 33.750 ± 40.285 | 4 | 0.500 ± 0.577 | 4 | 3.750 ± 6.850 |
| 1 day after $4^{th}$ administration | 4 | 0.750 ± 0.500 | 4 | 3.000 ± 2.708 | 4 | 0.500 ± 0.577 | 4 | 1.250 ± 0.500 |
| 3 days after $4^{th}$ administration | 4 | 0.250 ± 0.500 | 4 | 0 ± 0 | 4 | 0 ± 0 | 4 | 0 ± 0 |
| 7 days after $4^{th}$ administration | 4 | 0.250 ± 0.500 | 4 | 6.750 ± 12.842 | 4 | 1.000 ± 0 | 4 | 1.750 ± 1.258 |
| 10 days after $4^{th}$ administration | 4 | 0 ± 0 | 4 | 8.500 ± 16.340 | 4 | 0.250 ± 0.500 | 4 | 2.000 ± 2.828 |
| 14 days after $4^{th}$ administration | 4 | 6.750 ± 7.089 | 4 | 33.500 ± 19.689 | 4 | 1.500 ± 0.577 | 4 | 9.500 ± 8.699 |
| 18 days after $4^{th}$ administration | 4 | 48.000 ± 24.993 | 4 | 54.750 ± 4.031 | 4 | 14.000 ± 6.00. | 4 | 32.000 ± 13.638 |

In the specification, descriptions with reference to the terms "an embodiment", "some embodiments", "examples", "specific examples", or "some examples", etc., mean specific features, structures, materials or characteristics described in conjunction with the embodiment or example are included in at least one embodiment or example of the present disclosure. In this specification, the above terms are illustrative, and do not necessarily refer to the same embodiment or example. Moreover, the described specific features, structures, materials or characteristics can be combined in a suitable manner in any one or more embodiments or examples. In addition, those skilled in the art can combine the different embodiments or examples and the features of the different embodiments or examples described in this specification without contradicting each other.

SEQUENCE LISTING

```
Sequence total quantity: 7
SEQ ID NO: 1            moltype = AA  length = 298
FEATURE                 Location/Qualifiers
REGION                  1..298
                        note = 1
source                  1..298
                        mol_type = protein
                        organism = synthetic construct
SEQUENCE: 1
TYKKNDEVEF VRTGYGKDMI KVLHIQRDGK YHSIKEVATT VQLTLSSKKD YLHGDNSDVI  60
PTDTIKNTVN VLAKFKGIKS IETFAVTICE HFLSSFKHVI RAQVYVEEVP WKRFEKNGVK  120
HVHAFIYTPT GTHFCEVEQI RNGPPVIHSG IKDLKVLKTT QSGFEGFIKD QFTTLPEVKD  180
RCFATQVYCK WRYHQGRDVD FEATWDTVRS IVLQKFAGPY DKGEYSPSVQ KTLYDIQVLT  240
LGQVPEIEDM EISLPNIHYL NIDMSKMGLI NKEEVLLPLD NPYGKITGTV KRKLSSRL    298

SEQ ID NO: 2            moltype = AA  length = 304
FEATURE                 Location/Qualifiers
REGION                  1..304
                        note = 2
source                  1..304
                        mol_type = protein
                        organism = synthetic construct
SEQUENCE: 2
MAHYRNDYKK NDEVEFVRTG YGKDMIKVLH IQRDGKYHSI KEVATSVQLT LSSKKDYLHG  60
DNSDVIPTDT IKNTVNVLAK FKGIKSIETF AVTICEHFLS SFKHVIRAQV YVEEVPWKRF  120
EKNGVKHVHA FIYTPTGTHF CEVEQIRNGP PVIHSGIKDL KVLKTTQSGF EGFIKDQFTT  180
LPEVKDRCFA TQVYCKWRYH QGRDVDFEAT WDTVRSIVLQ KFAGPYDKGE YSPSVQKTLY  240
DIQVLTLGQV PEIEDMEISL PNIHYLNIDM SKMGLINKEE VLLPLDNPYG RITGTVKRKL  300
TSRL                                                                304

SEQ ID NO: 3            moltype = AA  length = 297
FEATURE                 Location/Qualifiers
```

-continued

```
REGION                  1..297
                        note = 3
source                  1..297
                        mol_type = protein
                        organism = synthetic construct
SEQUENCE: 3
MYKNDEVEFV RTGYGKDMVK VLHIQRDGKY HSIKEVATSV QLTLSSKKDY VYGDNSDIIP  60
TDTIKNTVHV LAKFKGIKSI ETFAMNICEH FLSSFNHVIR AQVYVEEVPW KRFEKNGVKH  120
VHAFIHNPTG THFCEVEQMR SGPPVIHSGI KDLKVLKTTQ SGFEGFIKDQ FTTLPEVKDR  180
CFATKVYCKW RYHQGRDVDF EATWDTVRDI VLEKFAGPYD KGEYSPSVQK TLYDIQVHSL  240
SRVPEMEDME ISLPNIHYFN IDMSKMGLIN KEEVLLPLDN PYGKITGTVK RKLSSRL     297

SEQ ID NO: 4            moltype = AA  length = 304
FEATURE                 Location/Qualifiers
REGION                  1..304
                        note = 4
source                  1..304
                        mol_type = protein
                        organism = synthetic construct
SEQUENCE: 4
MAHYHNDYKK NDEVEFVRTG YGKDMVKVLH IQRDGKYHSI KEVATSVQLT LSSKKDYVYG  60
DNSDIIPTDT IKNTVHVLAK FKGIKSIETF AMNICEHFLS SFNHVIRAQV YVEEVPWKRF  120
EKNGVKHVHA FIHNPTGTHF CEVEQMRSGP PVIHSGIKDL KVLKTTQSGF EGFIKDQFTT  180
LPEVKDRCFA TKVYCKWRYH QGRDVDFEAT WDTVRDIVLE KFAGPYDKGE YSPSVQKTLY  240
DIQVHSLSRV PEMEDMEISL PNIHYFNIDM SKMGLINKEE VLLPLDNPYG RITGTAKRKL  300
ASKL                                                               304

SEQ ID NO: 5            moltype = AA  length = 304
FEATURE                 Location/Qualifiers
REGION                  1..304
                        note = 5
source                  1..304
                        mol_type = protein
                        organism = synthetic construct
SEQUENCE: 5
MAHYHNDYQK NDEVEFVRTG YGKDMVKVLH IQRDGKYHSI KEVATSVQLT LNSRREYLHG  60
DNSDIIPTDT IKNTVQVLAK FKGIKSIETF AMNICEHFLS SFNHVIRVQV YVEEVPWKRF  120
EKNGVKHVHA FIHTPTGTHF CEVEQLRSGP PVIHSGIKDL KVLKTTQSGF EGFLKDQFTT  180
LPEVKDRCFA TQVYCKWRYH QGRDVDFEAT WEAVRGIVLK KFAGPYDKGE YSPSVQKTLY  240
DIQVLSLSQL PEIEDMEISL PNIHYFNIDM SKMGLINKEE VLLPLDNPYG RITGTVKRKL  300
TSRL                                                               304

SEQ ID NO: 6            moltype = AA  length = 304
FEATURE                 Location/Qualifiers
REGION                  1..304
                        note = 6
source                  1..304
                        mol_type = protein
                        organism = synthetic construct
SEQUENCE: 6
MAHYHNDYKK NDEVEFVRTG YGKDMVKVLH IQRDGKYHSI KEVATSVQLT LSSKKDYLHG  60
DNSDIIPTDT IKNTVHALAK FKGIKSIEAF AVNICQHFLS SFNHVIRTQV YVEEIPWKRL  120
EKNGVKHVHA FIHTPTGTHF CEVEQLRSGP PVIHSGIKDL KVLKTTQSGF EGFIKDQFTT  180
LPEVKDRCFA AQVYCKWRYH QCRDVDFEAT WDTIRDVVLE KFAGPYDKGE YSPSVQKTLY  240
DIQVVSLSQV PEIDDMEISL PNIHYFNIDM SKMGLINKEE VLLPLDNPYG KITGTVKRKL  300
SSRL                                                               304

SEQ ID NO: 7            moltype = AA  length = 304
FEATURE                 Location/Qualifiers
REGION                  1..304
                        note = 7
source                  1..304
                        mol_type = protein
                        organism = synthetic construct
SEQUENCE: 7
MADYHNNYKK NDELEFVRTG YGKDMVKVLH IQRDGKYHSI KEVATSVQLT LSSKKDYLHG  60
DNSDIIPTDT IKNTVHVLAK FKGIKSIEAF GVNICEYFLS SFNHVIRAQV YVEEIPWKRL  120
EKNGVKHVHA FIHTPTGTHF CEVEQLRSGP PVIHSGIKDL KVLKTTQSGF EGFIKDQFTT  180
LPEVKDRCFA TQVYCKWRYH QCRDVDFEAT WGTIRDLVLE KFAGPYDKGE YSPSVQKTLY  240
DIQVLSLSRV PEIEDMEISL PNIHYFNIDM SKMGLINKEE VLLPLDNPYG KITGTVKRKL  300
SSRL                                                               304
```

What is claimed is:

1. A method for preparing a polyethylene glycol-modified urate oxidase, characterized by performing a coupling reaction between urate oxidase and polyethylene glycol to obtain the polyethylene glycol-modified urate oxidase, wherein the polyethylene glycol is provided in a form of an acidic solution, and a molar ratio of the urate oxidase to the polyethylene glycol is 1: (56 to 94).

2. The method according to claim 1, wherein the acidic solution contains at least one selected from organic acids and/or inorganic acids.

3. The method according to claim 2, wherein the organic acids are selected from acetic acid, oxalic acid, maleic acid, tartaric acid, citric acid, succinic acid, malonic acid, adipic acid, ascorbic acid, benzenesulfonic acid, benzoic acid, butyric acid, cyclopentylpropionic acid, digluconic acid, dodecylsulfuric acid, ethanesulfonic acid, formic acid, fumaric acid, glucoheptonic acid, glycerophosphoric acid, gluconic acid, heptanoic acid, hexanoic acid, 2-hydroxyethanesulfonic acid, digalacturonic acid, lactic acid, lauric acid, laurylsulfuric acid, malic acid, malonic acid, methanesulfonic acid, 2-naphthalenesulfonic acid, nicotinic acid, oleic acid, palmitic acid, pectic acid, 3-phenylpropionate, picrate, pivalic acid, propionic acid, stearic acid, p-toluenesulfonic acid, undecanoic acid, or pentanoic acid; and the inorganic acids are selected from hydrochloric acid, hydrobromic acid, phosphoric acid, sulfuric acid, perchloric acid, hydriodic acid, nitric acid, persulfuric acid, boric acid, dichromic acid, silicic acid, chromic acid, or thiocyanic acid.

4. The method according to claim 2, wherein a concentration of hydrogen ions in the acidic solution ranges from 1 mmol/L to 5 mmol/L.

5. The method according to claim 2, wherein the acidic solution contains hydrochloric acid, sulfuric acid, or glacial acetic acid.

6. The method according to claim 5, wherein a concentration of the acid in the acidic solution ranges from 1 mmol/L to 5 mmol/L.

7. The method according to claim 1, wherein a concentration of the polyethylene glycol in the acidic solution ranges from 100 mmol/L to 300 mmol/L.

8. The method according to claim 1, wherein the polyethylene glycol has a molecular weight of not more than 6 KD; or the polyethylene glycol has a monomethoxy group or a hydroxyl group; or the polyethylene glycol is of a linear or branched structure; or the polyethylene glycol is coupled to the urate oxidase via an amide bond.

9. The method according to claim 1, wherein the polyethylene glycol is a modifying polyethylene glycol, and a modification group of the modifying polyethylene glycol is at least one selected from the group consisting of N-hydroxysuccinimide, N-hydroxysuccinimidyl carbonate, N-hydroxysuccinimidyl acetate, N-hydroxysuccinimidyl propionate, N-hydroxysuccinimidyl butyrate, N-hydroxysuccinimidyl succinate, and bis(p-nitrophenyl) carbonate.

10. The method according to claim 9, wherein the modification group of the modifying polyethylene glycol is N-hydroxysuccinimide propionate.

11. The method according to claim 1, wherein the coupling reaction is performed in a carbonate buffer solution, wherein the carbonate buffer solution has a pH of 9 to 11.

12. The method according to claim 1, wherein a concentration of the urate oxidase in a coupling reaction system is 10 mg/ml.

13. The method according to claim 1, wherein the coupling reaction is performed at 5° C. to 30° C. for at least 60 min.

14. The method according to claim 1, wherein at least 11 of the following amino acid sites in the urate oxidase have a PEG modification:

$T^{1}$, $K^{3}$, $K^{4}$, $K^{30}$, $K^{35}$, $K^{76}$, $K^{79}$, $K^{97}$, $K^{112}$, $K^{116}$, $K^{120}$, $K^{152}$, $K^{179}$, $K^{222}$, $K^{231}$, $K^{266}$, $K^{272}$, $K^{285}$, $K^{291}$, $K^{293}$, wherein the amino acid sites are positioned based on an amino acid sequence set forth as SEQ ID NO: 1.

15. The method according to claim 1, wherein the urate oxidase has an amino acid sequence set forth as any one of SEQ ID NOs: 1 to 7; or the urate oxidase is a polypeptide having at least 70%, at least 75%, at least 80%, at least 85%, at least 90%, at least 95%, or at least 99% identity with any one of SEQ ID NOs: 1 to 7.

16. The method according to claim 15, wherein the urate oxidase has an amino acid sequence set forth as any one of SEQ ID NOs: 1 to 4.

17. The method according to claim 1, wherein at least one of the following four amino acid sites of the polyethylene glycol-modified urate oxidase has a PEG modification:

$K^{30}$, $K^{35}$, $K^{222}$, and $K^{231}$, wherein the amino acid sites are positioned based on an amino acid sequence set forth as SEQ ID NO: 1.

18. The method according to claim 1, wherein peak areas of at least 11 predetermined peptide fragments in a peptide map of the polyethylene glycol-modified urate oxidase are reduced by a relative proportion of 75% or more.

19. The method according to claim 18, wherein the peptide map of the polyethylene glycol-modified urate oxidase has the peptide fragments with peak area reduction and relative proportions of reduced peak areas of the peptide fragments listed below:

| Peptide fragment position | Peptide fragment sequence | Relative proportion of reduced peak area of peptide fragment |
|---|---|---|
| 1-3 | TYK | 100.00% |
| 4-12 | KNDEVEFVR | 94.07% |
| 31-35 | YHSIK | 100.00% |
| 75-76 | FK | 82.27% |
| 80-97 | SIETFAVTICEHFLSSFK | 100.00% |
| 102-112 | AQVYVEEVPWK | 100.00% |
| 113-116 | RFEK | 100.00% |
| 117-120 | NGVK | 100.00% |
| 121-152 | HVHAFIYTPTGTHFCE VEQIRNGPPVIHSGIK | 100.00% |
| 193-197 | YHQGR | Internal reference peptide fragment |
| 198-209 | DVDFEATWDTVR | Internal reference peptide fragment |
| 216-222 | FAGPYDK | 91.37% |
| 223-231 | GEYSPSVQK | 86.40% |
| 232-266 | TLYDIQVLTLGQVP EIEDMEISL PNIHYLNIDMSK | 100.00% |
| 273-285 | EEVLLPLDNPYGK | 100.00% |

20. The method according to claim 18, wherein the peptide map of the polyethylene glycol-modified urate oxidase is shown in FIG. 6 or FIG. 7.

* * * * *